United States Patent
Jayaraman

(10) Patent No.: US 11,571,254 B2
(45) Date of Patent: Feb. 7, 2023

(54) DEVICE FOR LAPAROSCOPIC SURGERY

(71) Applicant: Shiva Jayaraman, Toronto (CA)

(72) Inventor: Shiva Jayaraman, Toronto (CA)

(*) Notice: Subject to any disclaimer, the term of this patent is extended or adjusted under 35 U.S.C. 154(b) by 1377 days.

(21) Appl. No.: 15/749,388

(22) PCT Filed: Jul. 29, 2016

(86) PCT No.: PCT/CA2016/050906
§ 371 (c)(1),
(2) Date: Jan. 31, 2018

(87) PCT Pub. No.: WO2017/214700
PCT Pub. Date: Dec. 21, 2017

(65) Prior Publication Data
US 2018/0221084 A1    Aug. 9, 2018

(30) Foreign Application Priority Data
Jul. 31, 2015 (CA) .................................. CA2899017

(51) Int. Cl.
*A61B 18/14*     (2006.01)
*A61B 18/12*     (2006.01)
(Continued)

(52) U.S. Cl.
CPC .......... *A61B 18/1482* (2013.01); *A61B 18/12* (2013.01); *A61M 1/774* (2021.05);
(Continued)

(58) Field of Classification Search
CPC ............... A61B 18/1482; A61B 18/12; A61B 2018/00196; A61B 2018/00208;
(Continued)

(56) References Cited

U.S. PATENT DOCUMENTS 4,061,146 A     12/1977     Baehr et al.
4,955,882 A *    9/1990     Hakky .................. A61B 18/24
                                                            606/14
(Continued)

FOREIGN PATENT DOCUMENTS

EP           2792321 A1    10/2014
WO      200150965 A2    7/2001

OTHER PUBLICATIONS

International Search Report and Written Opinion, regarding PCT/CA2016/050906, completed Sep. 28, 2016.
(Continued)

*Primary Examiner* — Jaymi E Della
(74) *Attorney, Agent, or Firm* — Aird & McBurney LP

(57) ABSTRACT

A surgical device which combines cautery and tissue debris conveyance via a combination of suction and an Archimedes screw, the cautery electrode encased within the Archimedes screw, the device comprising a device body housing a motor for rotating the screw, a cannula having an aperture for exposing an instrument, extending from the body portion, and a connector system operatively associated with the body portion, the connector system organized to provide predetermined relative locations of connection for operably connecting the cannula, a cautery electrode and an Archimedes screw to the device body such the cautery electrode tip is positionable outside the aperture of the cannula and the Archimedes screw is disposed within the cannula in a position for conveying tissue entering the cannula via suction.

29 Claims, 9 Drawing Sheets

(51) Int. Cl.
*A61M 1/00* (2006.01)
*A61B 17/00* (2006.01)
*A61B 18/00* (2006.01)

(52) U.S. Cl.
CPC .............. *A61B 2017/00685* (2013.01); *A61B 2018/00196* (2013.01); *A61B 2018/00208* (2013.01); *A61B 2018/00595* (2013.01); *A61B 2018/00928* (2013.01); *A61B 2018/00958* (2013.01); *A61B 2018/1475* (2013.01); *A61B 2218/002* (2013.01); *A61B 2218/007* (2013.01)

(58) Field of Classification Search
CPC ........... A61B 2018/00595; A61B 2018/00928; A61B 2018/00958; A61B 2018/1475; A61B 2218/002; A61B 2218/007; A61B 2017/00685; A61M 1/774
See application file for complete search history.

(56) References Cited

U.S. PATENT DOCUMENTS

| | | | |
|---|---|---|---|
| 5,312,400 A | 5/1994 | Bales et al. | |
| 5,348,555 A | 9/1994 | Zinnanti | |
| 5,395,312 A | 3/1995 | Desai | |
| 5,431,650 A * | 7/1995 | Cosmescu | A61B 18/1402 606/41 |
| 5,591,187 A * | 1/1997 | Dekel | A61B 17/32002 606/180 |
| 8,096,957 B2 | 1/2012 | Conquergood et al. | |
| 8,317,727 B2 | 11/2012 | Peliks | |
| 8,795,278 B2 | 8/2014 | Schmitz et al. | |
| 8,920,448 B2 | 12/2014 | To et al. | |
| 8,931,682 B2 | 1/2015 | Timm et al. | |
| 2005/0261676 A1 * | 11/2005 | Hall | A61B 18/1485 606/48 |
| 2006/0241586 A1 | 10/2006 | Wilk | |
| 2006/0253069 A1 * | 11/2006 | Li | A61M 37/00 604/93.01 |
| 2008/0103412 A1 * | 5/2008 | Chin | A61B 17/32002 606/15 |
| 2010/0076428 A1 | 3/2010 | Durgin et al. | |
| 2014/0276813 A1 * | 9/2014 | Gambrell | A61B 18/1482 606/49 |

OTHER PUBLICATIONS

Backlund, Erik-Olof and Von Holst, Hans, "Controlled Subtotal Evacuation of Intracerebral Haematomas by Stereotactic Technique" Surgical Neurology, 1978, vol. 9, No. 2, pp. 99-101.

Tanikawa, T. et al., "CT-guided Stereotactic Surgery for Evacuation of Hypertensive Intracerebral Hematoma" Applied Neurophysiology, 1985, vol. 48, pp. 431-439.

Samadani, Uzma and Rohde, Veit, "A review of stereotaxy and lysis for intracranial hemorrhage" Neurosurgery Review, 2009, vol. 32, pp. 15-22.

Higgins, Alfred C. and Nashold, Blain S., "Stereotactic Evacuation of Large Intracerebral Hematoma" Applied Neurophysiology, 1980, vol. 43, pp. 96-103.

Kandel, Edward I. and Peresedov, Vjacheslaw V., "Stereotactic Evacuation of Spontaneous Intracerebral Hematomas" Stereotactic and Functional Neurosurgery, 1990, vol. 54-55, pp. 427-431.

* cited by examiner

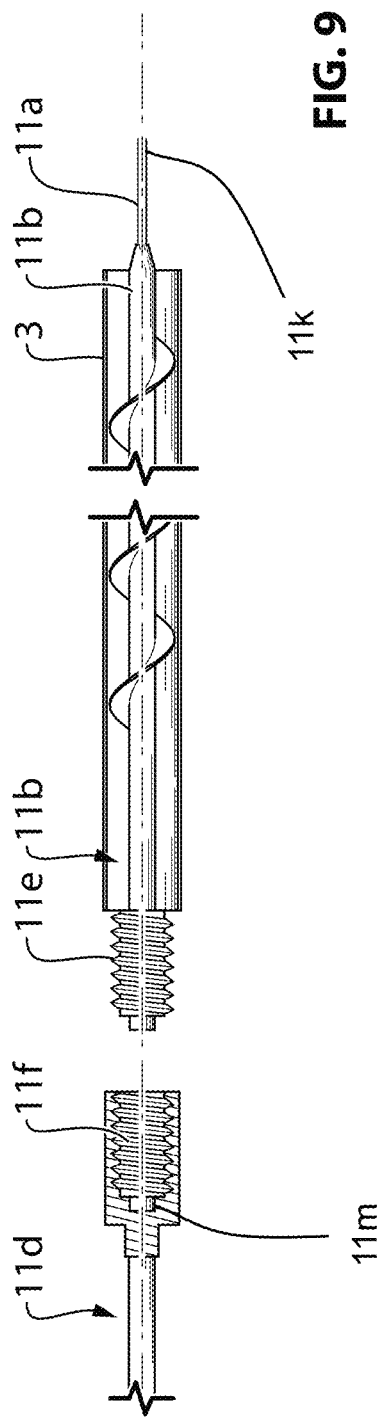

DEVICE FOR LAPAROSCOPIC SURGERY

CROSS-REFERENCE TO RELATED APPLICATIONS

This application is a national phase entry of PCT CA/2016/050906 filed Jul. 29, 2016, which claims the benefit of Canadian Patent Application No. CA2899017, filed Jul. 31, 2015, the contents of which are incorporated herein by reference in their entirety.

FIELD OF THE INVENTION

The present invention relates to a surgical device for performing surgery which combines energizing the tissue with an electrode and tissue debris conveyance via a combination of suction and an Archimedes screw.

BACKGROUND OF THE INVENTION

U.S. Pat. No. 5,348,555 ('555) describes an instrument for laparoscopic surgery including an instrument body and a cannula which combines cautery, aspiration and irrigation. The cautery rod is disposed within the cannula and can be manipulated so that it can be exposed (outside the cannula) or retracted to within the lumen of the cannula. The instrument body has finger-operated valves for respective connection to sources of suction and irrigation.

SUMMARY OF THE INVENTION

During minimally invasive surgery, for example laparoscopic surgery, suction may be applied to the end of the cannula to remove tissue debris and visual obstructions of the surgical field. Suction alone is sometimes ineffective to rapidly remove tissue debris such as blood clots as these clots can get trapped in the cannula, particularly in a standard size cannula of 5 mm in diameter.

The description herein is directed to a surgical device for surgery, for example laparoscopic surgery, that facilitates removal of blood clots and tissue debris.

The device is operable together with a cannula of an axial length and diameter which are generally standardized. In one example of a typical cannula of a type used for laparoscopic surgery an aperture at the mouth of the cannula of at least approximately 5 mm provides an opening through which an instrument (alternatively referred to as a tool) can be used to access the surgical field.

The device operably disposes an electrode tool, for example a cautery electrode and an Archimedes screw in the cannula and provides vacuum pressure from a vacuum source at the aperture. The screw has a hub and a flight.

According to one aspect, the disclosure herein is addressed to a surgical device, comprising:
 a surgical device body;
 a cannula extending from the surgical device body and having a proximal end and a distal end that is insertable into a surgical field within a patient, wherein the cannula defines an axis between the proximal and distal ends, wherein the cannula includes a vacuum port that is fluidically connectable to a vacuum source to draw material from the surgical field through the distal end into the cannula;
 an Archimedes screw positioned within the cannula and rotatable to transport material in the cannula towards the proximal end of the cannula, wherein the Archimedes screw has a hub and a flight; and a. an electrode tool that extends through the hub of the Archimedes screw and is movable between an advanced tool position and a retracted tool position, wherein in the advanced tool position a working end of the electrode tool is outside of the cannula and is energizable to energize tissue in the surgical field, and wherein in the retracted tool position the working end of the electrode tool is positioned axially closer to the proximal end of the cannula than in the advanced tool position so as to permit approach of the distal end of the cannula towards the tissue in the surgical field.

In one embodiment, the Archimedes screw is axially movable between an advanced screw position within the cannula and a retracted screw position, wherein in the advanced position the Archimedes screw is positioned closer to the distal end of the cannula than in the retracted position.

In one embodiment, the cautery tool is connected to the Archimedes screw such that when the screw is in the retracted screw position, the electrode tool is in the retracted tool position.

In one embodiment, the electrode tool is connected to the Archimedes screw such that when the screw is in the advanced screw position, the electrode tool is in the advanced tool position.

In one embodiment, in the retracted tool position, the working end of the cautery tool is substantially entirely held within the cannula.

In one embodiment, in the retracted tool position, the working end of the cautery tool is proximate the distal end of the cannula.

In one embodiment, the electrode tool is a cautery electrode.

In one embodiment, the cautery electrode is a monopolar electrode.

In one embodiment, the electrode tool is an RF electrode.

In one embodiment, the proximal end of the cannula (i.e. the proximal mouth of the cannula) is the vacuum port.

In one embodiment, the surgical device includes at a fluid conduit (also referred herein as a conduit portion) that is connectable between the vacuum port and the vacuum source.

In one embodiment, the surgical device further comprises a valve operable to initiate and terminate the application of vacuum pressure in the cannula.

In one embodiment, the cannula is outfitted with a vacuum port apart from the proximal mouth thereof. For example, the port may be a male or female connector configured to be attached to a fluid conduit e.g. in the form of the tube such that the vacuum port is fluidically connected to the vacuum source.

In one embodiment, the surgical device includes an actuator.

In one embodiment, the actuator is operable to move the electrode tool between an advanced tool position and a retracted tool position.

In one embodiment the actuator is manually operable to retract an electrode tool, for example by a surgeon pulling back a finger operable lever.

In one embodiment, the surgical device is a device for performing a laparoscopic surgery.

In one embodiment, the surgical device body is configured as a hand held device.

According to one aspect, the disclosure herein is addressed to a surgical device body, comprising:
 a housing having a cannula connector that is configured to releasably receive a cannula along an axis;

a drive system that is operable to cause rotation of a drive system output member, wherein the drive system output member has a first Archimedes screw connector that is connectable with a second Archimedes screw connector on an Archimedes screw so as to operatively connect the drive system to the Archimedes screw;

an electrical terminal that is positioned to electrically connect to a cautery tool that extends through a hub of the Archimedes screw;

wherein the drive system output member and the electrical terminal are axially movable between an advanced position and a retracted position relative to the housing.

Optionally, the electrical terminal is concentric with the cannula connector.

Optionally, first Archimedes screw connector is positioned concentrically with the first Archimedes with the electrical terminal.

According to one aspect, the disclosure herein is addressed to a surgical device body, comprising:

a housing having a cannula connector that is configured to releasably receive a cannula along an axis;

a drive system that is operable to cause rotation of a drive system output member, wherein the drive system output member has a first Archimedes screw connector connectable with a second Archimedes screw connector on an Archimedes screw so as to operatively connect the drive system to the Archimedes screw;

an electrical terminal that is positioned to electrically connect to a cautery tool that extends through a hub of the Archimedes screw;

wherein the electrical terminal is axially movable between an advanced position and a retracted position relative to the housing.

Optionally, the first Archimedes screw connector is positioned such that it is connectable with the second Archimedes screw only when the electrode tool is in the retracted position.

Optionally, the electrical terminal is positioned to bring the electrode tool to an advanced tool position in which the working end of the cautery tool is outside of the cannula.

According to another aspect, the disclosure herein is addressed to a surgical device body, comprising:

a housing having a cannula connector that is configured to releasably receive a cannula along an axis;

a drive system that is operable to cause rotation of a drive system output member, wherein the drive system output member has a first Archimedes screw connector that is connectable with a second Archimedes screw connector on an Archimedes screw so as to operatively connect the drive system to the Archimedes screw;

an electrical terminal that is positioned to electrically connect to an electrode tool that extends through a hub of the Archimedes screw;

an electrode tool connector configured to hold the electrode tool for axial movement therewith, the electrode tool connector movable between an advanced position and a retracted position relative to the housing.

Optionally, the electrode tool connector is positioned to bring the electrode tool to an advanced tool position in which the working end of the cautery tool is outside of the cannula.

Optionally, the first Archimedes screw connector is positioned such that it is connectable with the second Archimedes screw connector only when the electrode tool is in the retracted position. Where the electrode tool is connected to the Archimedes screw for movement therewith, the second Archimedes screw connector is movable between an advanced position and a retracted position relative to the housing. The first Archimedes screw connector and the second Archimedes screw connector are configured such that the latter is operable with the former only when the electrode tool is in the retracted position.

In one embodiment the device body further comprises fluid conduit that has a first conduit end that is fluidically connectable with a vacuum port on the cannula, wherein the fluid conduit is connectable with a vacuum source.

In one embodiment, the surgical device body is connected to a control system, the control system operable to control the drive.

In the one embodiment, the control system is operable to move the electrode tool connector between the advanced position and the retracted position.

In the one embodiment, the control system is operable to move the electrical terminal between the advanced position and the retracted position.

In the one embodiment, the control system is operable to move the first Archimedes screw connector between the advanced position and the retracted position.

In one embodiment, the surgical device body includes an actuator optionally for controlling movement between the advanced position and the retracted position.

In one embodiment, the control system controls the actuator.

In one embodiment, the control interface is operable to terminate operation of the electrode tool and contemporaneously initiate suction and rotation of the Archimedes screw. The control system is also operable to initiate operation of the electrode tool and preferably contemporaneously terminate suction.

According to one aspect, the disclosure is addressed to a method of carrying out a surgical procedure, comprising:
  a) providing a surgical device including a surgical device body, a cannula extending from the body and having a proximal end and a distal end, an Archimedes screw positioned in the cannula and having a hub and a flight, and an electrode tool that extends through the hub;
  b) inserting the cannula into a surgical field in a patient;
  c) providing the electrode tool in an advanced tool position in which a working end of the electrode tool is outside of the cannula;
  d) energizing tissue in the surgical field with the working end of the electrode tool;
  e) moving the electrode tool to a retracted tool position in which the working end of the electrode tool is positioned axially closer to the proximal end of the cannula than in the advanced tool position;
  f) manipulating the surgical device to bring the distal end of the cannula towards the tissue in the surgical field;
  g) applying a negative pressure in the cannula so as to draw material from the surgical field through the distal end into the cannula.
  h) rotating the Archimedes screw to transport material in the cannula towards the proximal end of the cannula.

In one embodiment step g) is carried out only when the cautery tool is in the retracted tool position.

In one embodiment step f) is carried out only when the cautery tool is in the retracted tool position.

In one embodiment, step h) is carried out only when the cautery tool is in the retracted tool position.

In one embodiment, the method further comprises:
  providing the Archimedes screw in an advanced screw position when the cautery tool is in the advanced tool position; and providing the Archimedes screw in a retracted screw position when the cautery tool is in the retracted tool position.

In one aspect, the disclosure is addressed to a kit of parts for a surgical device having a surgical device body, the kit of parts comprising:

a cannula releasably connectable to the surgical device body so as to extend from the surgical device body and having a proximal end and a distal end that is insertable into a surgical field within a patient, wherein the cannula defines an axis between the proximal and distal ends, wherein the cannula includes a vacuum port that is fluidically connectable to a vacuum source to draw material from the surgical field through the distal end into the cannula;

an Archimedes screw positionable within the cannula and rotatable to transport material in the cannula towards the proximal end of the cannula, wherein the Archimedes screw has a hub and a flight; and a cautery tool that extends through the hub of the Archimedes screw and is movable between an advanced tool position and a retracted tool position, wherein in the advanced tool position a working end of the cautery tool is outside of the cannula and is energizable to cauterize tissue in the surgical field, and wherein in the retracted tool position the working end of the cautery tool is positioned axially closer to the proximal end of the cannula than in the advanced tool position so as to permit approach of the distal end of the cannula towards the tissue in the surgical field.

In one embodiment, the kit of parts does not include the cannula.

The electrode tool may be linked to the Archimedes screw for rotation therewith. In this case, the control system is preferably operable to contemporaneously implement operation of the electrode tool, terminate suction, and terminate rotation of the Archimedes screw. Contemporaneous termination of rotation is optionally not mandatory and the user may be provided with an ability chose an alternative setting. Contemporaneous termination of rotation is optionally a default setting. Opting to allow rotation to continue after termination of suction would, for example, allow the circumferential orientation of an L-shaped or J-shaped cautery electrode tip (the shape of the electrode defining an orientable plane) to be selected.

The disclosure describes an embodiment in which the electrode tool and Archimedes screw are linked for axial movement. Optionally, the electrode tool and Archimedes screw are formed to be a single unit in which the electrode tool is embedded in the hub of the Archimedes screw. The disclosure describes this embodiment with specific reference to a cautery electrode which may be a monopolar electrode.

Optionally, the control system includes an actuator which functions to initiate and terminate the cautery function. In embodiment the actuator is operable between a treatment position in which the cautery electrode tip is outside the aperture and a shielded position in which the cautery electrode tip is axially withdrawn behind a perimeter of the aperture. The actuator is optionally a finger operated element which can be retracted and returned to position. Optionally, the screw is organized to travel with the cautery electrode and may be retracted contemporaneously. Nevertheless, in use, when the cautery electrode tip is in the shielded position, the conveyance-initiating end portion of the Archimedes screw is positioned at a distance behind the aperture which tissue debris will reach as a result of the application of suction pressure inside the cannula transmitted to the aperture.

One or more of the cannula, Archimedes screw and cautery may optionally be designed not to be removable, and if removable, optionally interchangeable or replaceable. In one embodiment, an instrument is constituted by a portion of the whole. For example, the screw and/or electrode may be constituted by a permanently attached part and a part remote from the body that is added, for example, by way of connection interface, for example in the form of male and female part that are joinable by a form of connector e.g. screwed together.

Thus, in one embodiment, the device, as sold, comprises a body portion that is pre-connected to a rod-shaped hollow cannula of a length and diameter usable in laparoscopic surgery. The device may further comprise an Archimedes screw instrument as described herein and the instrument is optionally provided attached or in parts with part attached. Optionally, the Archimedes screw instrument is not interchangeable (e.g. the device may be configured for one-time disposable use). Hence the connection interfaces between the body and the cannula and the body and the instrument may be more varied (particularly when assembled for sale connected) and some parts might be formed as partly integrated and partly removable.

In one embodiment, the device as sold comprises a body portion that is not connected to the cannula. The device includes a connector system. The connector system may provide a connection in the body or in the cannula.

The device optionally includes a drive mechanism (this device may also be external provided that a driven element connectable to the Archimedes screw instrument is provided) for rotating the Archimedes screw (e.g. a motor unit) and a port for connection to a monopolar supply. The device may further include a conduit system for applying suction at the aperture of the hollow cannula. Alternatively, the cannula itself has a port for attachment to an external source of suction. An external source of suction may be applied to a conduit system associated with the device or hollow cannula as the case may be or the device may include a dedicated source of vacuum pressure.

In either case, such a cannula typically has an interior wall portion defining a hollow channel and a longitudinal cannula axis through the center of the channel, a proximal end portion for connection to the body portion and a distal end portion having an aperture through which at least one instrument, receivable within the cannula, is exposable for treating a subject.

The connector system optionally includes a drive connection operable for drivably connecting a drive mechanism to the Archimedes screw (directly or indirectly), such that the drive mechanism is operable to rotate the Archimedes screw instrument in at least one direction, the at least one direction suitable for conveying material through the cannula towards the proximally located (proximal) end portion of the cannula.

Optionally, the cautery electrode is operatively associated with the Archimedes screw, for example securely integrated into the core of the Archimedes screw (to form a combined instrument which rotates and moves axially as one unit—sometimes referred to herein as an "Archimedes screw instrument") or freely disposed within the perimeter of the Archimedes screw, for example in a central hollow axial through hole therein.

In an Archimedes screw instrument the relative axial locations of the electrode tip (i.e. the portion thereof that is applied in practice to the tissue) of the cautery electrode and the conveyance-initiating portion of Archimedes screw are fixed i.e. their operative positions with respect to the axial location of the aperture. The Archimedes screw instrument includes an end portion for interfacing with the drive mechanism and a monopolar power supply at a location relatively proximal to the body i.e. relative to the distal location of a conveyance initiating portion of the Archimedes screw, the end portion operatively associated with a drivable element (alternatively called a driven element e.g. a gear), a distally located end portion for cautery and an intermediate portion exteriorly defining an Archimedes screw operable for conveying material through the cannula towards the proximal end portion of the cannula, the intermediate portion including a conveyance-initiating end-portion of the Archimedes screw located most proximally to the distally located end portion of the Archimedes screw instrument. A cautery electrode tip is provided at the distally located end portion of the Archimedes screw instrument. The end portion of the instrument is configured to provide conveyance-initiating end-portion of the Archimedes screw adjacent to the instrument end portion such that tissue debris reaches it as a result of the application of suction pressure inside the cannula transmitted to the aperture.

The Archimedes screw is connectable to a drive mechanism including a driving element via the driven element. The term connector may be used to refer to a driving element and the driven element may also be described as having a connector. The driven element provides a connection to the drive mechanism via the driving element e.g. a gear.

The drive mechanism, optionally a motor, is operable to rotate the Archimedes screw instrument in at least one direction, the at least one direction configured for conveying material through the cannula towards the proximal end portion of the cannula.

The device is optionally configured to be operatively connected to a conduit system comprising at least one conduit in fluid communication with respect to the cannula. The conduit system is understood to form part of a vacuum pressure system or an irrigation system. The at least one conduit serves to directly or indirectly (in conjunction with other conduits) connect the cannula to a source of vacuum pressure for applying suction to a surgical field via the distally located end portion of the cannula. Optionally, the at least one conduit is housed within the body. The at least one conduit may be directly connectable to the cannula outside the body portion of the device (the cannula is not necessarily part of the device as sold). Where the at least one conduit is located in the body portion of the device it may in turn be connected to male or female connector on the body portion of the device (e.g. such as a nipple) so the body portion can be directly connected via a length of conduit to a source of vacuum pressure (e.g. a wall suction port or suction generator).

The source of vacuum pressure is fluidically connectable to a receptacle for receiving suctioned material optionally via the conduit system.

Optionally, the source of vacuum pressure is accessed via a valve that is operably connected to at least one conduit, the valve operable between a first valve position for applying suction to the surgical field via the distal end of the cannula and a second valve position for terminating suction.

The device preferably includes at least one actuator, optionally a finger-operated actuator, optionally an actuator in the form of slidable trigger, the actuator is operable for preventing the cautery electrode from being operative when the source of vacuum pressure is engaged to provide vacuum pressure at the distal end of the cannula. The actuator is preferably operable to perform at least one of the following functions: a) withdraw the cautery electrode tip from a treatment position outside the cannula to a retracted position inside the cannula; b) switch off the monopolar generator; and c) interrupt the electrical connection between the cautery electrode and the monopolar generator. Operation of the actuator optionally also triggers the Archimedes screw instrument to rotate in the at least one direction.

The device includes a control system operatively associated with the source of vacuum pressure (e.g. the valve), the control system operable at least in part by the actuator, the actuator optionally is operatively associated with a switch that is operable to at least initiate and terminate suction, for example by operating the valve.

In use, the control system is optionally configured to rotate the Archimedes screw instrument in the at least one direction, contemporaneously draw material to the conveyance-initiating end portion of the Archimedes screw via suction, prevent the cautery electrode from being operative when the source of vacuum pressure is engaged e.g. by positioning the cautery electrode tip inside the cannula (e.g. positionally behind the cannula aperture). In use, the conveyance-initiating end portion of the Archimedes screw is positioned to receive material introduced into the aperture by suction.

According to one embodiment, the invention is directed to a device for performing laparoscopic surgery, the device operable in conjunction with a source of vacuum pressure for conveying tissue debris away from a surgical field, the device comprising:

A body portion operatively connectable to a rod-shaped cannula of a length and diameter sized for use in a laparoscopic surgery, the cannula preferably of the type including an interior wall portion defining a hollow channel and a longitudinal cannula axis, a proximal end portion for connection to the body portion and a distal end portion having an aperture through which at least one instrument receivable within the cannula is exposable outside the aperture for treating a subject, the linear distance between the proximal end portion of the cannula and the aperture defining a reference axial distance;

A connector system including at least one connector operatively associated with the body portion, the at least one connector organized to provide a connection for the cannula to the body portion and at least one second connection, the at least second connection operable for connecting a cautery electrode with respect to a monopolar generator and for drivably connecting a drive mechanism to an Archimedes screw such that the drive mechanism is operable to rotate the Archimedes screw instrument in at least one direction, the at least one direction suitable for conveying material through the cannula towards the proximal end portion of the cannula;

wherein the first connection and the at least one second connection are operably positioned at pre-determined relative axial locations for respective connection to a cannula; and to a cautery electrode and Archimedes screw of operative axial lengths with respect to the pre-determined relative axial locations of the first connection and the at least one second connection and the reference axial distance; such that a cautery electrode tip of the cautery electrode is positionable outside a perimeter of the aperture of the cannula and a conveyance initiating end-portion of the Archimedes screw is disposable within the cannula for rotation therein at a distance from the surgical field more remote from the surgical field than the cautery electrode tip and at a distance from the aperture operable for conveying tissue debris entering the cannula via the aperture towards the proximal end portion of the cannula;

wherein the device is operable with a control system for initiating and terminating suction and initiating and terminating cautery, the control system connectable to at least one of a source of vacuum pressure and a valve operable to initiate and terminate suction via a source of vacuum pressure, the control system operable in conjunction with a conduit system fluidically connectable to the cannula and the source of vacuum pressure for applying suction to a surgical field via the distal end portion of the cannula, the control system including at least one actuator, the at least one actuator operatively connected to the cautery electrode for implementing and disengaging cautery, the actuator operable between a first state for preventing cautery during suction, and a second state in which the cautery electrode is operable for cautery with the electrode tip exposed outside the aperture, the actuator operable for at least one of:

(a) moving the cautery electrode tip axially within the cannula along an axis parallel to the cannula axis, between a treatment position wherein at least a portion of the cautery electrode tip is disposed for use outside the perimeter of the aperture and a shielded position in which the cautery electrode tip withdrawn into the cannula inside the perimeter of the aperture;

(b) interrupting the electrical connection between the cautery electrode and the monopolar generator;

(c) turning the monopolar generator off wherein, in use:

the control system operable to draw tissue debris to the conveyance-initiating end portion of the Archimedes screw via suction when the cautery electrode is disengaged by the actuator.

The device optionally includes a drive mechanism. The drive mechanism is optionally a motor. The power supply for the motor is optionally a battery. The battery is optionally rechargeable. The motor is optionally housed within the body portion. The battery is optionally housed with the body portion.

According to another embodiment, the description herein is directed to a device for performing laparoscopic surgery, the device operable in conjunction with a source of vacuum pressure for conveying tissue debris away from a surgical field, the device comprising:

A body portion operatively connectable to a rod-shaped cannula of a length and diameter sized for use in a laparoscopic surgery, the cannula preferably of the type including an interior wall portion defining a hollow channel and a longitudinal cannula axis, a proximal end portion for connection to the body portion and a distal end portion having an aperture through which at least one instrument receivable within the cannula is exposable outside the aperture for treating a subject, the linear distance between the proximal end portion of the cannula and the aperture defining a reference axial distance;

A connector system including at least one connector operatively associated with the body portion, the at least one connector organized to provide a connection for the cannula to the body portion and at least one second connection, the at least second connection operable for connecting a cautery electrode with respect to a monopolar generator and for drivably connecting a drive mechanism to an Archimedes screw such that the drive mechanism is operable to rotate the Archimedes screw instrument in at least one direction, the at least one direction suitable for conveying material through the cannula towards the proximal end portion of the cannula;

wherein the first connection and the at least one second connection are operably positioned at relative axial locations for respective connection to a cannula of a selected axial length, and to a cautery electrode and Archimedes screw of operative axial lengths with respect to the relative axial locations of the first connection and the at least one second connection and the reference axial distance such that a cautery electrode tip of the cautery electrode is positionable outside a perimeter of the aperture of the cannula and a conveyance initiating end-portion of the Archimedes screw is disposable within the cannula for rotation therein at a distance from the surgical field more remote from the surgical field than the cautery electrode tip and at a distance from the aperture operable for conveying tissue debris entering the cannula via the aperture towards the proximal end portion of the cannula;

at least one actuator operatively connected to the cautery electrode for moving the cautery electrode axially within the cannula along an axis parallel to the cannula axis, the actuator operable between a treatment position in which at least a distal end portion of the cautery electrode tip is disposed for use in the surgical field, outside the perimeter of the aperture, and a shielded position in which the cautery electrode tip is axially withdrawn behind the perimeter of the aperture;

wherein, in the shielded position, the conveyance-initiating end portion of the Archimedes screw is positioned behind the perimeter of the aperture and behind the cautery electrode tip to receive tissue debris introduced into the aperture by vacuum pressure inside the cannula at the aperture.

The device for performing laparoscopic surgery as described above optionally further comprises any combination of the one or more the elements and/or features described herein.

A few such further features are described immediately below.

Optionally, in the shielded position, the conveyance-initiating end portion of the Archimedes screw is positioned at a distance behind the perimeter of the aperture which is approximately no greater than the axial distance required to move the portion of the cautery electrode tip disposed outside the aperture when in the treatment position, into the shielded position. Optionally, this distance is no greater than 4 to 5 mm.

Optionally, the device further comprises a control system, the control system including a control interface operable for at least initiating and terminating suction and initiating and terminating cautery (e.g. via turning the monopolar generator on and off or opening and closing the circuit that connects the cautery electrode tip to the monopolar generator or both), the control system connectable to at least one of the source of vacuum pressure and a valve operable to initiate and terminate suction in conjunction with the source of vacuum pressure, the control system operable in conjunction with a conduit system fluidically connected to the cannula and the source of vacuum pressure for applying suction to a surgical field via the distal end portion of the cannula, the control system operable to draw material to the conveyance-initiating end portion of the Archimedes screw via suction when the cautery electrode in the shielded position.

Optionally, the control system is operable to initiate suction only when the cautery electrode is in the shielded position.

Optionally, the control system is operable to control a drive mechanism optionally a motor.

Optionally, the device further comprises a drive mechanism. The drive mechanism, optionally a motor, may be provided as a separate module, for example a snap-on module, that is configured for attachment to the body portion of the device. For example the device may have an externally disposed drive connection interface that exposes a driven element adapted for connection to a driving element on the module. The module may include a battery or the module may be connectable to a separate power source. Optionally, the module may serve to partially define a hand piece for ease of manipulation of the device.

Alternatively, the driving element may be provided via a cable interface that connects the driving element to a more remotely located drive mechanism. The cable encloses an elongated optionally flexible drive shaft.

Alternatively, in one embodiment described in detail below, the drive mechanism, preferably a motor, is located in the body portion of the device.

According to one embodiment, the description herein is directed to a device for performing laparoscopic surgery, the device operable in conjunction with a source of vacuum pressure for conveying tissue debris away from a surgical field, the device comprising:

A body portion operatively connected to a rod-shaped cannula of a length and diameter sized for use in a laparoscopic surgery, the cannula preferably of the type including an interior wall portion defining a hollow channel and a longitudinal cannula axis, a proximal end portion for connection to the body portion and a distal end portion having an aperture through which at least one instrument receivable within the cannula is exposable outside the aperture for treating a subject, the linear distance between the proximal end portion of the cannula and the aperture defining a reference axial distance;

An instrument disposed within the cannula, the instrument including a cautery electrode and Archimedes screw, the cautery electrode linked to the Archimedes screw for rotation therewith;

A motor located in the body portion, the motor drivably connected to the instrument;

A connector system including at least one connector operatively associated with the body portion, the at least one connector organized to provide a connection for the motor to a power source and at least one second connection, the at least second connection operable for connecting a cautery electrode with respect to a monopolar generator and for drivably connecting the motor to the instrument such that the motor is operable to rotate the instrument in at least one direction, the at least one direction suitable for conveying material through the cannula towards the proximal end portion of the cannula;

wherein the cautery electrode and the Archimedes screw are of operative axial lengths with respect to the axial position of the at least one second connection and the reference axial distance such that a cautery electrode tip of the cautery electrode is positionable outside a perimeter of the aperture of the cannula and a conveyance initiating end-portion of the Archimedes screw is disposable within the cannula for rotation therein at a distance from the surgical field more remote from the surgical field than the cautery electrode tip and at a distance from the aperture operable for conveying tissue debris entering the cannula via the aperture towards the proximal end portion of the cannula;

a control system including a control interface for initiating and terminating suction, initiating and terminating rotation of the instrument, and initiating and terminating cautery, the control system connectable to the motor and to at least one of a source of vacuum pressure and a valve operable to initiate and terminate suction via a source of vacuum pressure, the control system operable in conjunction with a conduit system fluidically connectable to the cannula and the source of vacuum pressure for applying suction to a surgical field via the distal end portion of the cannula, the control system including at least one actuator, the at least one actuator operatively connected to the instrument for implementing and terminating cautery, the actuator operable at least between first state for preventing cautery during suction and a second state in which the cautery electrode is operable for cautery with the electrode tip exposed outside the aperture, the actuator operable for at least one of:

(a) moving the cautery electrode tip axially within the cannula along an axis parallel to the cannula axis, between a treatment position wherein at least a portion of the cautery electrode tip is disposed for use outside the perimeter of the aperture and a shielded position in which the cautery electrode tip withdrawn into the cannula inside the perimeter of the aperture;

(b) interrupting the electrical connection between the cautery electrode and the monopolar generator;

(c) turning the monopolar generator off and wherein, in use:

the control system operable to draw tissue debris to the conveyance-initiating end portion of the Archimedes screw via suction when cautery is terminated by the actuator.

The device for performing laparoscopic surgery as described above optionally further comprises any combination of the one or more the elements and/or features described herein.

A few such further features are described immediately below.

With respect to the embodiments described herein including a control system, it is to be appreciated that a device operably supporting a cautery electrode, an Archimedes screw and a cannula for use as broadly described herein, may be operative with an external control system and may therefore be sold independently of the external control system. An actuator for moving the cautery electrode between a treatment position and a shielded position is preferably operatively associated with the body of the device however other elements of the control interface may be provide on a separate control device as contemplated hereinbelow.

In the immediately ensuing paragraphs, the description herein is now directed to various aspects of a control device for use with a device operably supporting a cautery electrode, an Archimedes screw and a cannula for use as described herein.

In one aspect, a device comprising a control interface external to the body portion is provided for use with a laparoscopic device as defined above. The control interface may be embodied in a separate foot-operated or hand operated control device comprising one or more controls. A hand operated control interface may be partially presented in select aspects on a monitor for example a monitor used by a surgeon to visualize the laparoscopic procedure, for example a control that is usable after the instrument is ideally positioned as determined from the monitor. A control interface may include remotely control components including wirelessly operated and voice activated components.

The control system may include at least one control e.g. a switch for controlling a motor and at least one of: a source of vacuum pressure and a valve operable in conjunction with a source of vacuum pressure. A control device implementing a remotely located control system optionally includes a control (e.g. a physical switch) for controlling a connection from a monopolar generator to the cautery electrode. The device is optionally configured to provide an irrigation system (a connection for connecting a conduit carrying irrigation fluid to the cannula) and the control system accordingly includes a means for initiating and terminating irrigation. In one embodiment described in greatest detail below, the control system includes at least one finger operated control disposed on the device for operation by a user, for example the actuator described above and in detail below.

In one embodiment, a control system including a control interface is operable for at least initiating and terminating suction, initiating and terminating cautery and initiating and terminating operation of the drive mechanism, preferably a motor. The control system preferably contemporaneously initiates suction and rotation of the Archimedes screw in the at least one direction. The control system is preferably operable to initiate suction and rotation of the Archimedes screw only when the cautery is deactivated, for example when the cautery electrode tip of the cautery electrode is in a shielded position. The control system is optionally operable to move the cautery electrode tip into the shielded position and to contemporaneously initiate suction and rotation of the Archimedes screw. The control system is optionally operable to additionally contemporaneously disconnect power to the cautery electrode.

We describe, according to one aspect, a control mechanism including a control interface comprising means for contemporaneously initiating suction and initiating rotation of the Archimedes screw.

We describe, according to one aspect, a control mechanism including a control interface comprising means for contemporaneously initiating suction, initiating rotation of the Archimedes screw in the at least one direction and terminating an electrical connection to the cautery electrode.

The term "means" include a finger or foot operated switch or actuator and related components/circuitry. The term "means" also include a user interface on a screen.

As discussed above, the afore-described mechanisms may be embodied in a separate control device.

We describe, according to one aspect, a control mechanism including a control interface comprising means for contemporaneously—moving the cautery electrode tip of the cautery electrode from a treatment position to a shielded position, initiating suction, initiating rotation of the Archimedes screw and optionally terminating an electrical connection from a monopolar generator to the cautery electrode. We describe a control mechanism comprising a finger-operated actuator disposed on the body of the device that is operable as described. We describe means for initiating and terminating irrigation, optionally via a dedicated finger operated control e.g. a switch.

According to one aspect, we describe a control device operable to implement a control system as described herein.

The control device optionally includes a control interface and optionally includes means for initiating and terminating suction, initiating and terminating rotation of a motor in the at least one direction and initiating and terminating cautery. The device comprises or is connectable to at least one of the source of vacuum pressure and a valve operable to initiate and terminate suction in conjunction with the source of vacuum pressure. The device is operable in conjunction with a conduit system fluidically connected to the cannula and the source of vacuum pressure for applying suction to a surgical field via the distal end portion of the cannula. The conduit system optionally comprises a conduit portion that is directly fluidically connectable to the cannula, for example to a nipple located on a proximal end of the cannula outside the body portion of the device. Alternatively, the conduit system comprises a conduit portion that is fluidically connectable to the cannula via a connection on the body portion of the device. The control system is operable to draw material to the conveyance-initiating end portion of the Archimedes screw via suction when the cautery electrode in the shielded position. The device is preferably operable to contemporaneously initiate suction and rotation of the Archimedes screw in the at least one direction. The device is preferably operable to initiate suction and rotation of the Archimedes screw only when the cautery electrode tip of the cautery electrode is in a shielded position. The control system is optionally operable to additionally contemporaneously disconnect power to the cautery electrode.

The disclosure herein contemplates that a cautery electrode is a device adapted to generate tissue debris that at least partially controls the size of components of the tissue debris such that the combination of an Archimedes screw and suction improve the ability to remove the debris through a cannula.

It may be appreciated from the disclosure herein that the control system is simplified when a single control (e.g. an actuator optionally embodied as finger operated trigger) is used to perform multiple functions that are generally intended to be performed contemporaneously. Accordingly, these functions may be grouped to be initiated via a single control. The operations include deactivating cautery, optionally by withdrawing the cautery electrode tip in a shielded position and/or disconnecting power to the cautery electrode, initiating suction and initiating rotation of the Archimedes screw in the at least one direction. It may be appreciated that the same or different control elements may be used to terminate functions that are designated to be implemented when cautery is deactivated and restore cautery depending on whether they are to be performed as a group. For example, activating cautery by moving the cautery electrode tip into a treatment position might be invariably coupled to turning suction off particularly if the electrical connection to the cautery electrode is restored. Activating cautery by moving the cautery electrode tip into a treatment position might not be invariably restoring the electrical connection and terminating rotation if as described below it is desirable to rotate the cautery electrode together with the Archimedes screw to re-orient the position of the cautery electrode tip. Many permutations of the various functions that may be grouped and ungrouped will be apparent to those skilled in the art upon reading the disclosure herein and the description herein contemplates permutations that are not expressly disclosed.

The immediately ensuing description herein is now addressed to various embodiments of tools/instruments that provide for the ability to generate debris and safely remove the debris without clogging a cannula so that device can be used by a surgeon for a prolonged period without removal by reason of clogging.

The description herein contemplates that the cautery electrode is receivable in a hollow axial channel in the Archimedes screw and movable axially therein. The axial position of the Archimedes screw is optionally fixed and unchangeable when the cautery electrode is moved from the treatment position into the shielded position. Thus, the portion of the cautery electrode tip most proximal to the surgical field (in the case of an L hook the portion of the hook that extends perpendicularly to cannula axis i.e. radially across the diameter of the cannula), is positionable more closely to the distal end of the screw. Thus when the cautery electrode tip is positioned behind the perimeter of the aperture of the cannula in the shielded position, the portion of the vane that defines the end of the screw is unchanged and maintains a position sufficiently proximal to the aperture to receive tissue debris introduced into the aperture by vacuum pressure inside the cannula at the aperture.

The radial orientation of the optional slot is optionally orthogonal to the plane defined by the portion of the vane that defines the end of the screw.

In one embodiment, described in detail below, the axial positions of the conveyance-initiating portion of the Archimedes screw and cautery electrode tip cannot be changed by the actuator independently of one another, for example, if the cautery electrode is immovably encased in the core of the Archimedes screw. In this embodiment, the conveyance-initiating portion of the Archimedes screw is axially withdrawn together with the cautery electrode when the combined instrument is axially retracted into the shielded position. In the shielded position, the vane that defines the end of the screw becomes re-positioned further behind the perimeter of the aperture.

Optionally, in an enhanced embodiment of the combined instrument the vane that defines the end of the screw is positioned as closely as possible to the axially most distal end the cautery electrode tip.

Optionally, the first connection and the at least one second connection are operable for respective connection at selected relative axial positions that accommodate a cannula of a selected axial length, and a combined instrument of a corresponding relative length that minimizes the distance between the most distal end the cautery electrode tip and the perimeter of the aperture in the treatment position. As described below, the linear axial travel distance of the actuator between the treatment position and the shielded position is optionally configured accordingly.

BRIEF DESCRIPTION OF THE DRAWINGS

FIG. 9 is a diagram showing an optional connector for an electrode screw tool.

DETAILED DESCRIPTION OF PREFERRED EMBODIMENT

Figure 1:
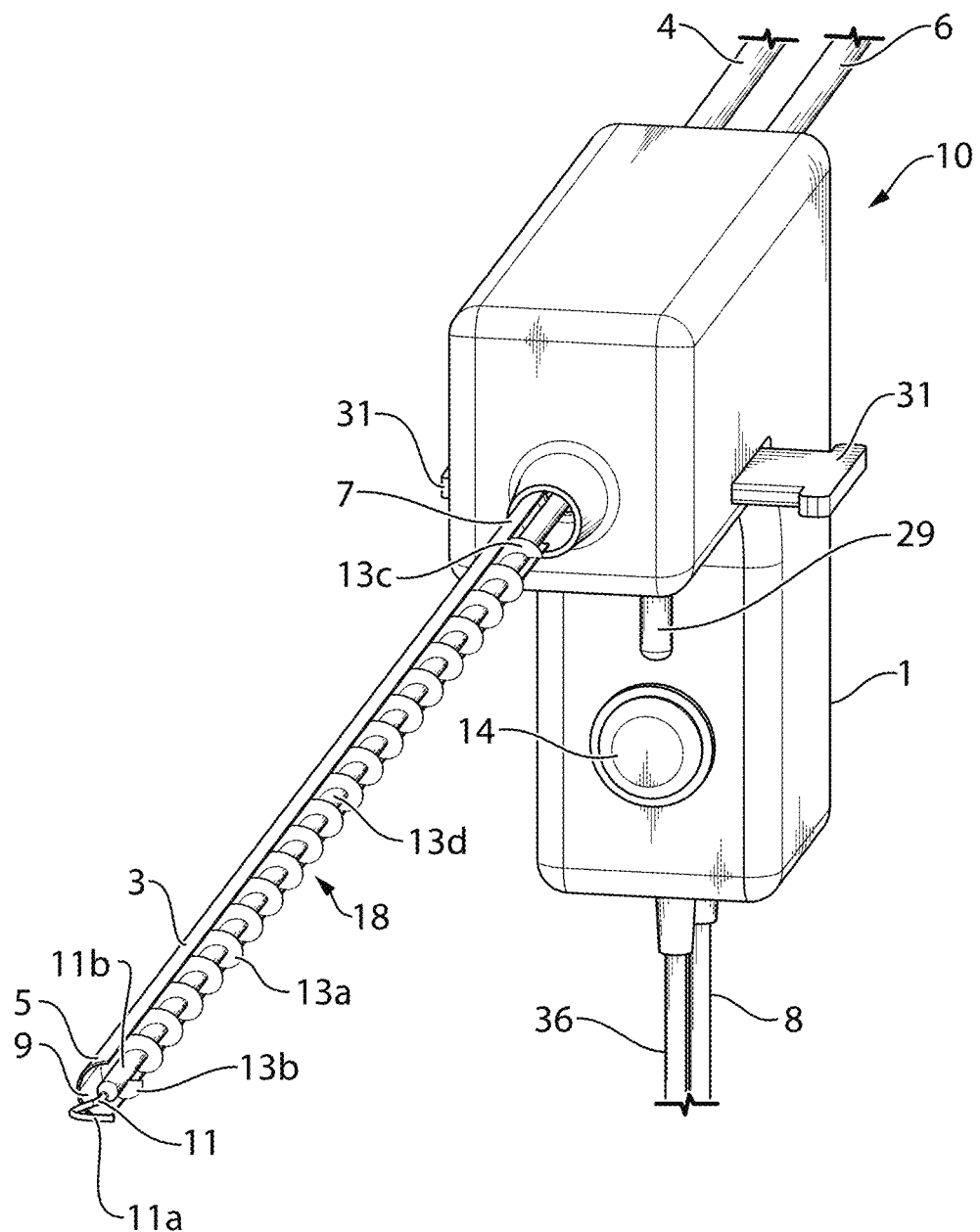
FIG. 1 is a front perspective view of a device according to one embodiment of the invention in which one embodiment of a surgical tool is shown together with one embodiment of a surgical device body in the form of a hand held device, in this embodiment a device configured to be used to provide cautery and debris removal with a combination of suction and conveyance via an Archimedes screw in a laparoscopic surgical setting. Key accessory components—a cannula, an Archimedes screw and electrode tool (embodied in the form of a cautery electrode) are shown and the Archimedes screw and electrode tool as illustrated as a combined electrode-screw tool referred to as an Archimedes screw instrument.

Many of the features and embodiments described in the disclosure herein and in the claims herein (either as individual limitations within a claim or grouped limitation forming a whole claim) with respect to a particular embodiment of a surgical device and a surgical device body (also referred to as a body portion) in the form a device for laparoscopic surgery (illustrated as hand held device) are understood to be relevant and individually disclosed in a more general context to a surgical device in which the electrode tool is not limited to a cautery electrode and the surgical device body is not part of hand held device but rather a mechatronic or robotic arm. The surgical device and surgical device body may be used in connection with a mechatronic or robotic system in which the control system is and one or more associated control interfaces are remotely positioned at a dedicated work station for operation by a surgeon. A vacuum port may be provided directly on the cannula. The mechatronic arm in some current systems does not have an internal fluid conduit that is in fluid communication with a vacuum source or a valve for controlling air flow through the fluid conduit. In the embodiment described in detail herein the surgical device body often referred to a body portion is a part of device which is hand held and hence can be accommodated with integrated parts such a fluid conduit and a valve. A kit of parts described above may be supplied for use with a surgical device body as generally described above whether part of a mechatronic/robotic device or a hand operated device and to compose elements of the surgical device as generally described above.

A portion of the Archimedes screw positioned near the aperture (generally the most distal part of the flight) may be described herein, for convenience as a conveyance-initiating end portion of the Archimedes screw. In one embodiment. This portion of the screw is positioned behind the aperture to receive tissue debris introduced into the aperture by vacuum pressure inside the cannula that is applied at the aperture.

In one embodiment, these features are integrated into a surgical device body minimally comprising a body portion and a connector system to which a hollow cannula and tools or instruments are connectable as described herein.

The connector system is operatively connected to the surgical device body. The connector system includes at least one connector, the at least one connector (one or more connectors), configured for connection to the hollow cannula, to the Archimedes screw and to the electrode tool. The hollow cannula has a proximal end, sometimes referred to as a first end portion or first cannula end portion for connecting it to the body and a second end portion (sometimes referred to herein as the second cannula end portion) providing an aperture for accessing the surgical field. The Archimedes screw has a first end proximal to the body and a second end distal from the body for receiving tissue debris from the surgical field via the aperture.

The electrode tool, optionally in the form of a cautery electrode, has a first end portion for connecting to the at least one connector (sometimes referred to herein as a first electrode end portion) and a second end portion (sometimes referred to herein as the second electrode end portion) terminating in/carrying an electrode tip for accessing the surgical field via the aperture. The connector system positions the second end of the cautery electrode and the second of the Archimedes screw at operative positions with respect to the aperture. The distance that the tip (i.e. the portion thereof that is applied in practice to the tissue) of the electrode tool and the terminal end of the flight portion (also referred to as conveyance-initiating portion of Archimedes screw) respectively extend, in an axial direction, in relation to the aperture (the mouth of the cannula) i.e. the relative axial positions of the most distal portions of these components are determined by the connection system which axially (parallel to the longitudinal axis of the cannula) positions the working ends of these components in functional relation to one another. The operative relative lengths of the cannula, Archimedes screw and cautery electrode are adapted to the connection system (and vice versa) and to their operative positions in relation to one another.

The device body referred to as a surgical device body, and in one embodiment, a body portion, provides connections to the cannula, cautery electrode, the Archimedes screw. The term "connection" particularly when used to refer to the connector system e.g. for connecting accessory device components directly or indirectly to the body portion, in particular cannula 3, cautery electrode 11 and Archimedes screw 13, is used to mean a functional interface suitable for any single or any combination of functions requiring contact including holding or supporting a device component, positioning the device component, contacting the device component (e.g. electrically), interfacing with the device component for a function other than specified e.g. for drivably operating a device component (driving or being driven by). In principle, a plurality of functions may be achieved by a single connection e.g. holding and positioning, holding and electrically contacting, etc. In principle, a single connector may provide a plurality of interfaces and/or accomplish a variety of functions. The description herein contemplates the optional use of rotating electrical connectors, rotating fluid connectors etc. In principle, a rotating electrical connector may be configured to be driven (e.g. if operably linked to a driven element) so that in principle it could perform the functions of electrically contacting, being driven by, driving something else (an Archimedes screw instrument), positioning and supporting.

"Connection" to the body portion means to any or more of (any permutation) the body portion itself, to a structure operably located within the body portion, or to a structure attached to the body portion. Similarly, a connection to the Archimedes screw means to any one or more of (any permutation) the Archimedes screw itself, a structure operably located within the Archimedes screw, a structure attached to the Archimedes screw, etc. In general, the terms "connect to" and "connection to" and related terms are broadly construed as being of a type that is direct or indirect with the proviso only that the requisite function of the interface is directly or indirectly accomplished.

As described below, the electrode tool in the form of a cautery electrode 11 and Archimedes screw 13 are optionally combined in to a single instrument 18. This combined instrument is optionally "held" (supported) at one interface or point of connection, electrically connected at a second interface or point of connection, and rotated at a third interface or point of connection. A connection or interface may be performing any combination of these functions. All of these types of interface are individually referred to herein using the term "connection" or similar and related terms e.g. "connect", "link" and "interface". The term "Archimedes screw instrument" is used to refer to an instrument having exterior vanes configured as a screw that is connected to a cautery electrode for rotation therewith. The term Archimedes screw is used more broadly to refer to an instrument that is not defined by whether or not it is connected for rotation with the cautery electrode, the instrument having an elongated structure of a selected length having an exterior surface defining an Archimedes screw over at least a portion of its length. An Archimedes screw has a proximal end portion remotely positioned from the surgical field and distal end portion defining a conveyance-initiating end portion of the screw. The screw optionally comprises a hollow channel for receiving a cautery electrode.

The phrase "inside the perimeter", used with reference to an aperture at the end of the cannula through which an instrument is exposed, means in a position behind the mouth of the aperture.

The term "cautery electrode tip" means that portion of the cautery electrode intended for contact with the tissue of a patient, that is not encased in a sheath. As mentioned below, in one embodiment, the sheath is optionally made of the same material as the Archimedes screw and the cautery electrode is optionally encased within the core of the screw. The cautery electrode and Archimedes screw optionally rotate together. In a preferred embodiment, the linear axial distance (along an axis parallel to the axis of the cannula) between the end of the sheath and the most distal end of the cautery electrode tip is kept small so that the conveyance-initiating end of the Archimedes screw (the most distal portion of the external vane defining the screw) can be formed onto or connected to sheath of the cautery electrode. This in turn keeps the distance between the conveyance-initiating end of the Archimedes screw and the periphery of the aperture small when the screw is axially retracted so that tissue debris has a short travel distance under the influence of suction alone before the screw participates in conveyance of the debris.

The connector system organized to provide relative locations of connection for connection of the cannula, a cautery electrode and an Archimedes screw to the body portion. The connector system includes a drive connection interface operable for drivably connecting a drive mechanism to an Archimedes screw instrument when disposed within the cannula. The connector system includes an electrode connection interface for connecting a monopolar generator to the cautery electrode. The connector system preferably provides for pre-determined relative positioning of the drive connection interface, electrode connection interface and cannula. The connector system optionally provides for a separately manufactured cannula to be attached to the body portion. Where the device is sold without a pre-attached cannula the connector system is configured to allow the cannula to be securely connected to the body portion, optionally in a removable fashion, for example using a disengageable locking system of variable type, an example of which is described below.

In one embodiment, in the retracted tool position, the working end of the cautery tool is substantially entirely held within the cannula. This position is alternatively referred to as a shielded position. The advanced is alternatively referred to as a treatment position.

The surgical device body is also referred to as a body or body portion. The term hand held device is also referred to as a hand piece.

The term vacuum source is alternatively referred to as a source of vacuum pressure.

As seen in FIG. 1, according to one embodiment, device 10 includes a surgical device body in the form of body portion 1 that is optionally shaped in the form of a hand piece suitable for laparoscopic surgery. A cannula 3 (shown partially broken away) is connected to the body portion 1 via a proximal end portion of the cannula 7. A cautery electrode tip 11a may be exposed via an aperture 9 located in a distal end portion 5 of cannula 3.

The body portion 1 includes a connection interface to an external source of suction (not shown) which is optionally implemented via a conduit 4. A conduit connection port may be provided on or within the body portion. For example, conduit 4 is optionally connected at one end to a nipple (not shown) on the body portion 1 and at the other end to an aspiration port located in a wall of a surgical suite (not shown).

The body portion 1 optionally includes a connection interface to an external source of irrigation fluid (not shown) which is implemented via a conduit 6. A conduit connection port for conduit 6 may be provided on or within the body portion. For example, conduit 6 is optionally connected at one end thereof to a nipple on the body portion (not shown) and at the other end to an irrigation pump associated with an irrigation fluid reservoir (not shown). Irrigation is initiated with finger operated switch 14.

As seen in FIG. 1, the body portion 1 includes a connection interface for connecting device 10, via wire 8, to an electrode power supply in the form of a monopolar generator, the monopolar generator operable to supply power to cautery electrode 11. A power supply cable 36 may be provided to charge a battery housed within body portion 1, as described with reference to FIG. 2.

The cannula 3 is preferably non-conductive and may be made of plastic. Optionally, the cannula 3 is transparent. A transparent cannula may be made of a variety of materials, for example, polyvinyl chloride or acrylic.

The electrode-screw tool in the form of Archimedes screw instrument 18 is disposed in cannula 3 by a connector system described in more detail below.

Archimedes screw instrument 18 comprises an Archimedes screw portion 13 and a cautery electrode portion 11. The plastic sheath 13d encasing the cautery electrode 11 is constructed to provide a flight in the form an external vane 13a that defines the operative interface of the Archimedes screw 13. The Archimedes screw 13 includes a most distal part of the flight in the form of conveyance-initiating portion 13b and proximal end portion 13c. Optionally, the cautery electrode tip 11a is an L-hook that lies in a plane that this is generally aligned with a plane defined by the leading edge of the conveyance-initiating portion 13b of the screw so as better accommodate uptake of debris by the conveyance-initiating portion 13b of the Archimedes screw 13.

As seen in FIG. 1, an actuator 29 extends from the body portion 1. Actuator 29 may be a finger-operated switch, trigger or lever. The actuator is optionally operatively connected to a locking mechanism, for example, in the form of locking element 31 which can be accessed by a user's thumb or index finger from both sides of the body portion 1, thereby accommodating both right and left-handed use.

As will now be described with reference to FIG. 2, actuator 29 is operatively connected to valve 12 and motor 21, for contemporaneously initiating suction and rotation of the Archimedes screw, respectively, and to the cautery electrode 11, for interrupting its electrical connection (turning the electrode "off").

Optionally, the actuator is a mechanical trigger 29 that is connected to and retracts the cautery electrode from an advanced tool position (also referred to as an advanced position or with reference to the electrode specifically a treatment position) and contemporaneously engages switch 19. In the embodiment shown in the Figures, the actuator 29 is a finger-operated lever or trigger 29. Trigger 29 is operatively connected to the structure encasing the cautery electrode 11 via a linkage interface 50, so that the exposed cautery electrode tip 11a may be withdrawn into a retracted tool position also referred to a retracted position which is optionally a shielded position within an interior perimeter of cannula 3, optionally a retracted position within the lumen of cannula 3 via aperture 9, when suction is applied to the surgical field as described hereafter with reference to FIG. 4. This feature is desirable for patient safety so that the negative pressure created by suction does not inadvertently draw the cautery electrode into contact with tissue and cause tissue damage.

The cautery electrode 11 is commonly shielded in a plastic sheath 11b. The electrode toll in form of the cautery electrode 11 be may a separate instrument that is slidably receivable in a longitudinal channel (embodiment not illustrated) in the Archimedes screw 13. In the embodiment illustrated in the Figures, Archimedes screw instrument 18 integrates the structures of the cautery electrode 11 and the Archimedes screw 13 and therefore sheath 11b corresponds to sheath 13d.

An insulating sheath is provided on parts of the electrode housed within the body. Thus interfacing parts such as the linkage interface 50, gear 52 and switch 19 may be conductive or may be non-conductive e.g. these interfacing parts may be made of plastic.

Figure 2:
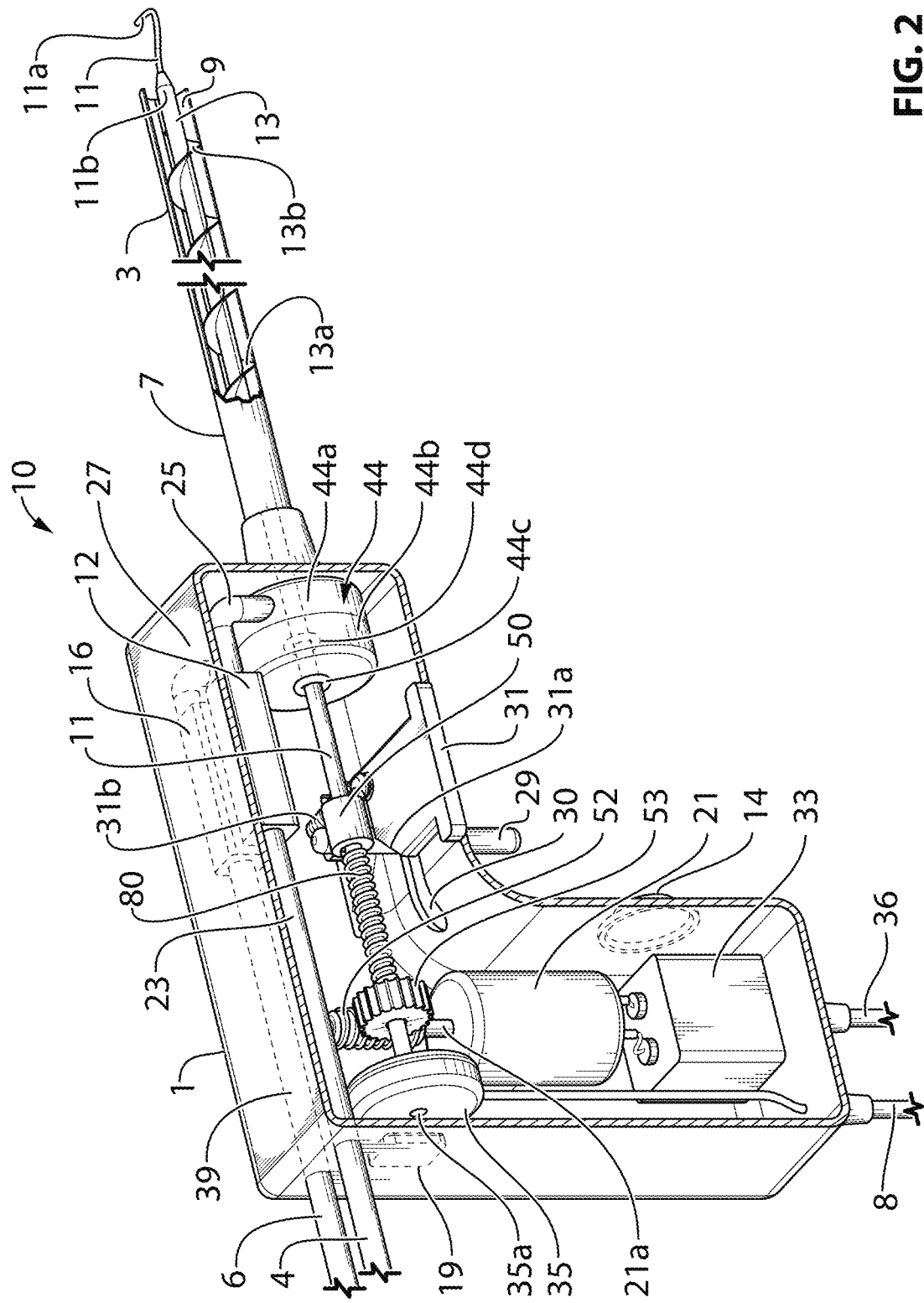
FIG. 2 is a cross-sectional side perspective view of the surgical device body with accessory parts attached according to the embodiment shown in FIG. 1.

As seen in FIG. 2, actuator 29 is a short rod that is mounted for slidable movement within slot 30 and positioned to be retracted with an index finger. The actuator 29 is biased to occupy a forward position by compression spring 80 which corresponds with a "treatment position" or "second position" of the cautery electrode 11.

Disengageable locking element 31, embodied in form of an irregularly shaped plate locks the actuator 29 in a retracted (rearward) position when the actuator 29 is pulled back with an index finger. Locking element 31 includes a slot 31a that allows the actuator 29 to slide forward. Locking element 31 is spring-biased (spring 31b) to occupy a locking position which moves the slot 31a out of alignment with the actuator 29 so as to prevent actuator 29 from returning to a forward position via slot 31a unless the user urges the locking element laterally to overcome the spring bias. This realigns the actuator 29 with slot 31a. Releasing actuator 31 allows the switch 19 is able to re-occupy an "off" position, as described in more detail hereafter.

It will be appreciated that an actuator in the form of a trigger could be used to rotate the Archimedes screw without a motor for example, using a spiral drive system (a type of mechanism used in yankee screw driver) for converting linear displacement of the trigger into rotation of the Archimedes screw in a single desired direction. For example, a first portion of the trigger travel distance could be used to withdraw the cautery electrode (and engage the lock mechanism) and a second portion to rotate the Archimedes screw uni-directionally so that repeated pulls on the trigger continuously advance the movement of tissue debris. In this case, the placement or operation of switch 19 would be organized accordingly.

Figure 4:
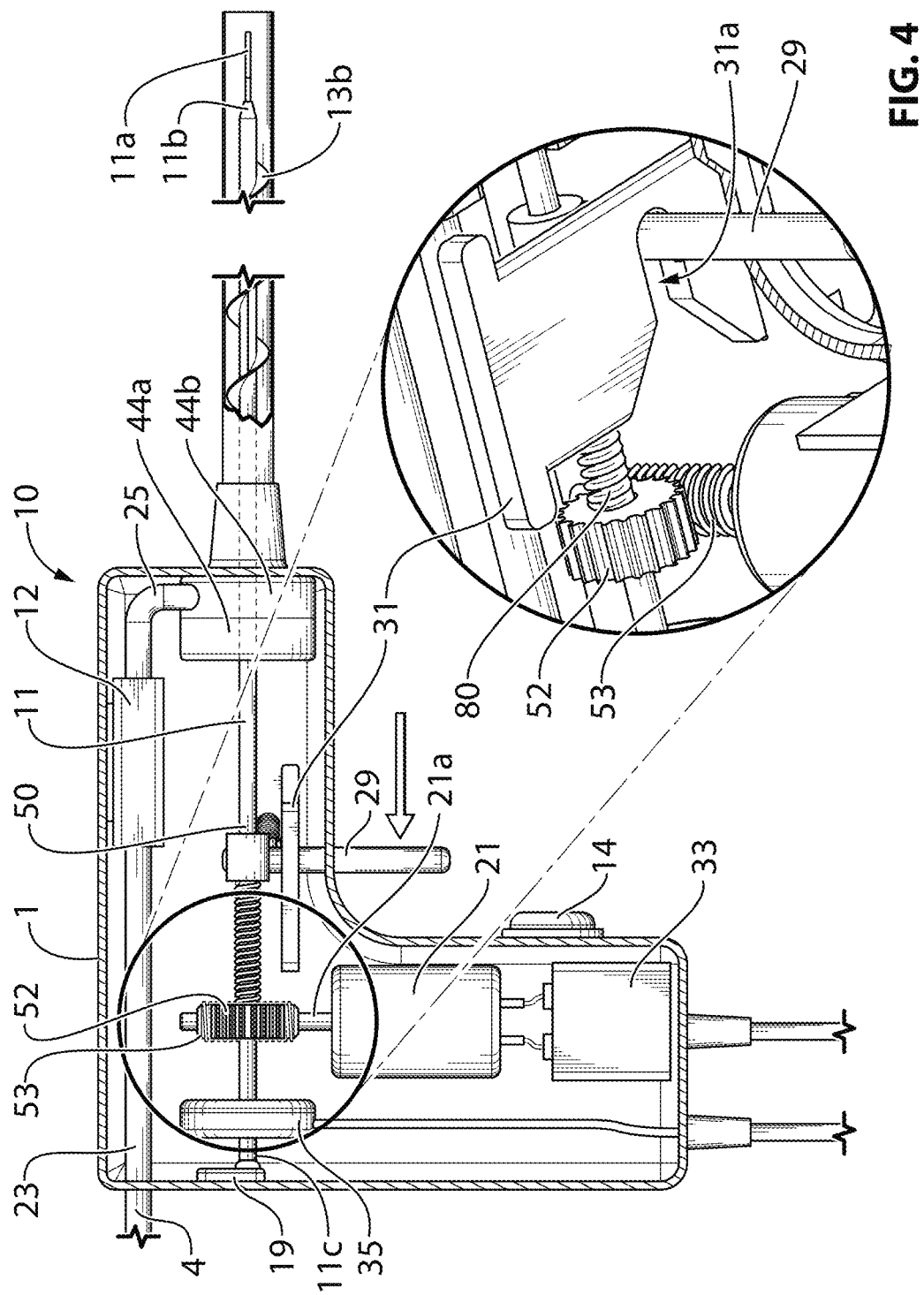
FIG. 4 is a cross-sectional side elevation of the surgical device body with accessory components attached according to the embodiment shown in FIG. 1 showing the actuator in a retracted position.

Actuator 29 is operatively linked to switch 19 albeit indirectly. Switch 19 is optionally of type operable to tripped mechanically by depressing the switch (other options magnetically, electronically etc.). For example, switch 19 is positioned to be mechanically engaged by an end portion of the electrode-screw tool in the form of Archimedes screw instrument 18. Mechanical activation of switch 19 may alternately be accomplished by providing any sort of switch abutting interface on the actuator, on the cautery electrode or on a plastic sheath encasing the cautery electrode, such that the interface is re-positioned to operatively contact the switch (for example a lever or push button type switch). In the embodiment shown in the Figures, as best seen in FIG. 4, rearwards displacement of the back end of Archimedes screw instrument 18 exposes the back end of cautery electrode 11c which emerges from aperture 35a in rotating connector 35 to engage switch 19.

Switch 19 is in turn operatively connected to a solenoid valve 12 (e.g. a valve from STC 2P025 Series) and motor 21 for both initiating suction and rotation of the Archimedes screw respectively, and is optionally connected to the cautery electrode electric circuit, as well, for interim interruption of its electrical connection to the monopolar generator 8. The drive system is shown as providing a motor 21 which (optionally) is in the body of the device, the drive system includes a drive shaft 21a and a gear 52 described below. The drive system optionally includes shaft 11d which includes a first Archimedes screw connector. A drive system output member which is connected to gear 53. Gear 52 operatively engages and drives a driven element in the form of gear 53 to convert rotation of the drive shaft 21a about its axis into rotation of gear 53 about an orthogonal axis.

Figure 3:
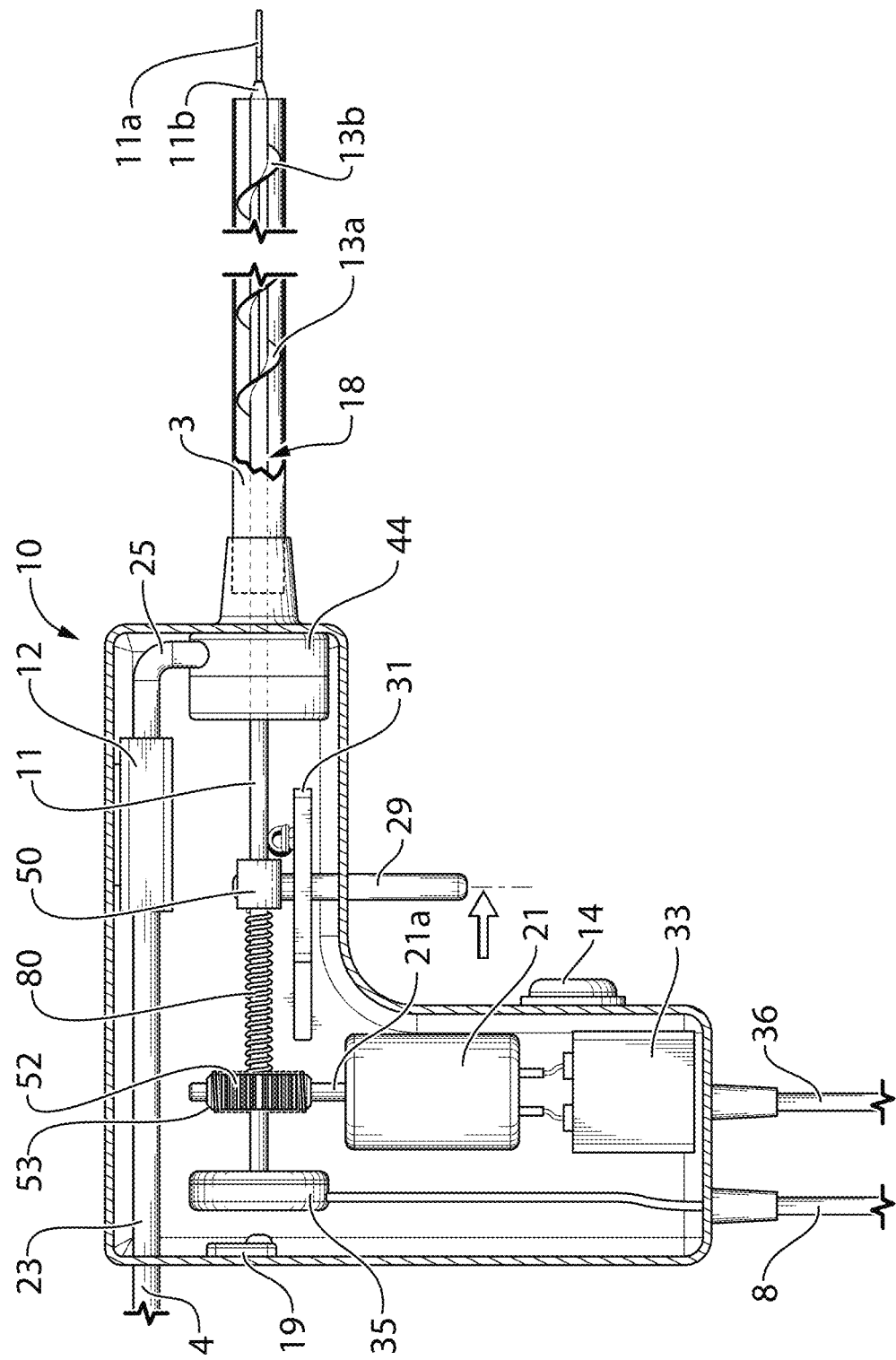
FIG. 3 is a cross-sectional side elevation of the surgical device body with accessory components attached according to the embodiment shown in FIG. 1, showing an actuator in a forward treatment position.

Referring to a surgical device body in a broader context, the surgical device body comprises a drive system that provides for an Archimedes screw optionally in the form of electrode-screw to connected to a tool by a user as opposed to being supplied with a tool already connected. As described in more detail below with reference to the Figures the drive system causes a drive system output member to be rotated. The drive system output member may be configured to provide a shaft 11d as shown in FIG. 9. In this embodiment, the first Archimedes screw connector is the threaded receptacle 11f and the second Archimedes screw connector is the threaded portion of 11b. The electrical terminal is optionally located in the shaft and is thus concentric with the drive system output member. The drive system output member may also provide a first Archimedes screw connector, in one embodiment in the form of a gear 52 at its end as shown in FIG. 2 and the second Archimedes screw connector is a gear 53. The electrical terminal alternatively be part of a rotating connector 35. The electrode tool connector optionally takes the form a linkage interface 50 that is connected to the combined electrode-screw tool for axial movement therewith. The combined electrode-screw tool may provide a cautery electrode for example a monopolar electrode. The linkage interface is optionally configured in the form a sleeve as shown in FIG. 3.

Suitable motors with compatible gearbox kits are readily available from a variety of sources (optional specification: 1.5-4.5 v; 1125:1 ratio, 3 mm shaft). The motor preferably operates efficiently at low voltages; motor output may optionally be 1430 RPM at 0.5 VDC and 4500 RPM at 1.5 VDC.

The motor may be a variable speed motor. The RPM of the motor 21 may be reduced with a potentiometer 125.

It will be appreciated that actuator 29 may serve to trip an appropriately connected switch in a variety of different ways to allow for contemporaneous initiation of suction and rotation of the Archimedes screw instrument.

In the embodiment of the device shown in Figures, the cautery electrode 11 and Archimedes screw 13 rotate together are these parts are integrated into one instrument 18. A rotating electrical connector 35, optionally a slip ring, maintains the electrical connection to the monopolar generator when the Archimedes screw rotates. When actuator's 29 is finger-actuated to withdraw the cautery electrode tip 11a into cannula 3, the end of the instrument engages switch 19 to turn the switch into an "on" position—namely a position in which it opens a normally closed solenoid valve and optionally initiates (if rotation is accomplished with a motor) rotation. It will be appreciated that switch 19 may alternatively turn on a suction generating device (as opposed to operating a solenoid valve for initiating suction from a pre-existing source of suction pressure).

As seen in FIG. 2, according to one embodiment of the invention, suction and irrigation are implemented via internal conduit portions 23 and 39, respectively, located within the body portion 1. Solenoid valve 12 is interposed between conduit portion 23 and conduit portion 25. Solenoid valve 12 is operable between a normally closed (NC) position to block wall suction and an open position to access wall suction. Conduit portion 25 is connected to the rotating connector 44 which is in turn fluidly connected to the open proximal portion 7 of cannula 3.

In the parallel irrigation circuit, solenoid valve 16 is interposed between conduit portion 39 and conduit portion 27. Solenoid valve 16 is operable between a normally closed position to prevent irrigation and an open position to effect irrigation. Conduit portion 27 is connected to the rotating connector 44 which is in turn connected to the open proximal portion 7 of cannula 3.

As seen in FIG. 2, the rotating connector 44 comprises a first portion 44a for receiving conduits 25 and 27. Portion 44a thus provides a stationary interface to connect suction and irrigation conduits respectively to the rotating connector. Portion 44a of the rotating connector 44 is sealingly connected for relative rotation to rotating portion 44b which rotates together with electrode 11. Rotating portion 44b is fluidly connected to the cannula. Electrode 11 is sealingly linked to portion 44b by a sealably mating interface including o-ring 44c and portions 44a and 44b are sealingly connected to one another by a sealingly mating interface including o-ring 44d so that fluid entering or leaving conduits 25 and 27 can flow backwards through this interface from rotating connector portion 44a into portion 44b and then into the cannula 3. Rotating connectors of this type are commonly used in a variety of applications.

It will be appreciated that a rotating connector is optional. For example, suction can be effected via a first connection port to the cannula 3 and irrigation effected via a second connection port to cannula 3, and cautery/rotation via a third connection axially aligned with the longitudinal axis of cannula 3, the connections for suction and irrigation positioned downstream (distally) relative the proximal open end of the cannula 3. Alternatively, all three individual connections can share a surface of a common manifold.

Figure 8:
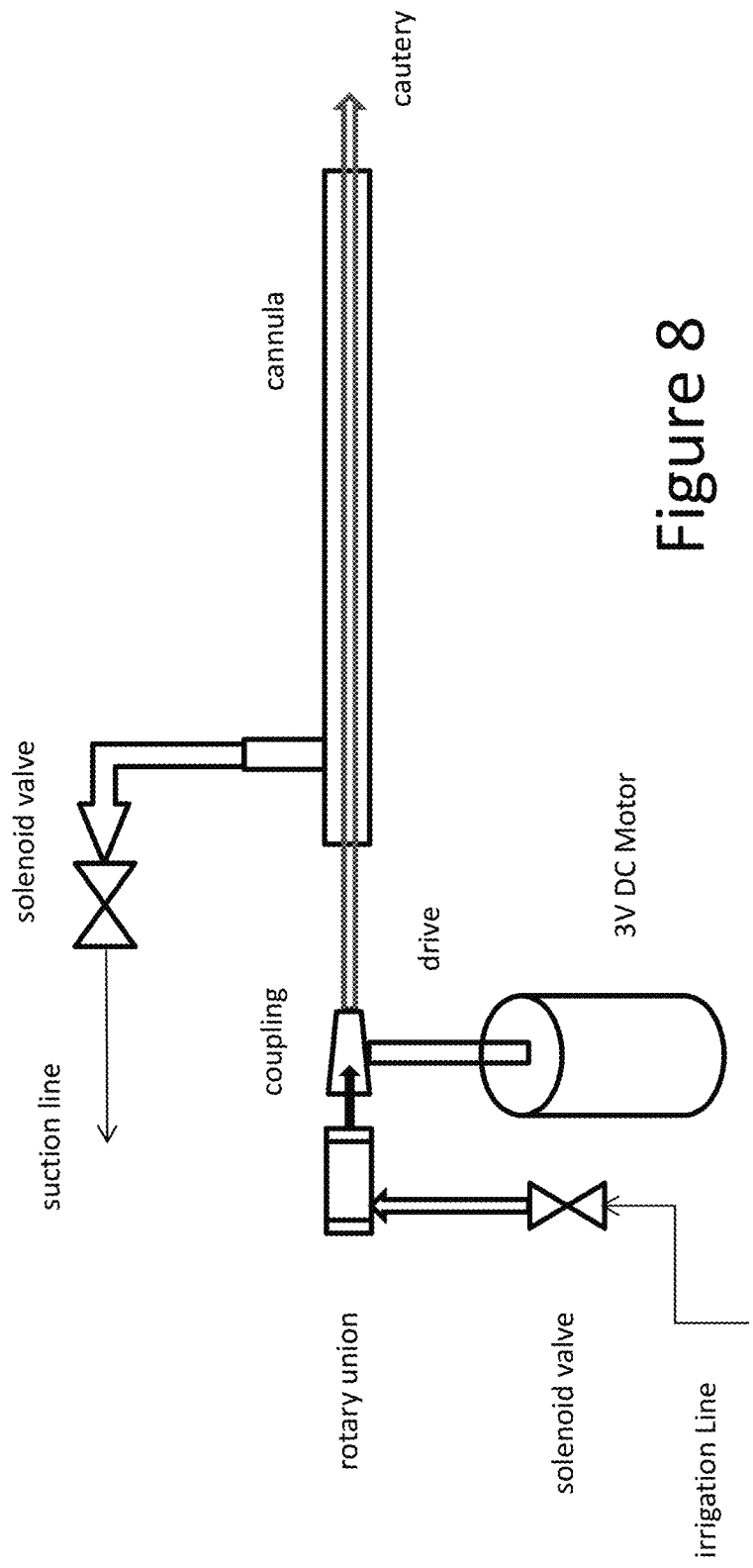
FIG. 8 is a schematic diagram showing an alternative scheme for connecting irrigation and suction conduits to the cannula for use with a rotating electrode-screw tool.

Alternatively, the connector to the cannula 3 for both irrigation and cautery can effected by an axially aligned rotating connector (for example a rotating connector of a type available from Deublin Company) and the connection to suction may located downstream from the proximal open end of cannula 3 as illustrated schematically in FIG. 8. In this schema, irrigation fluid flows around a rotating cautery electrode. Cautery is turned off when irrigation is used.

Figure 5:
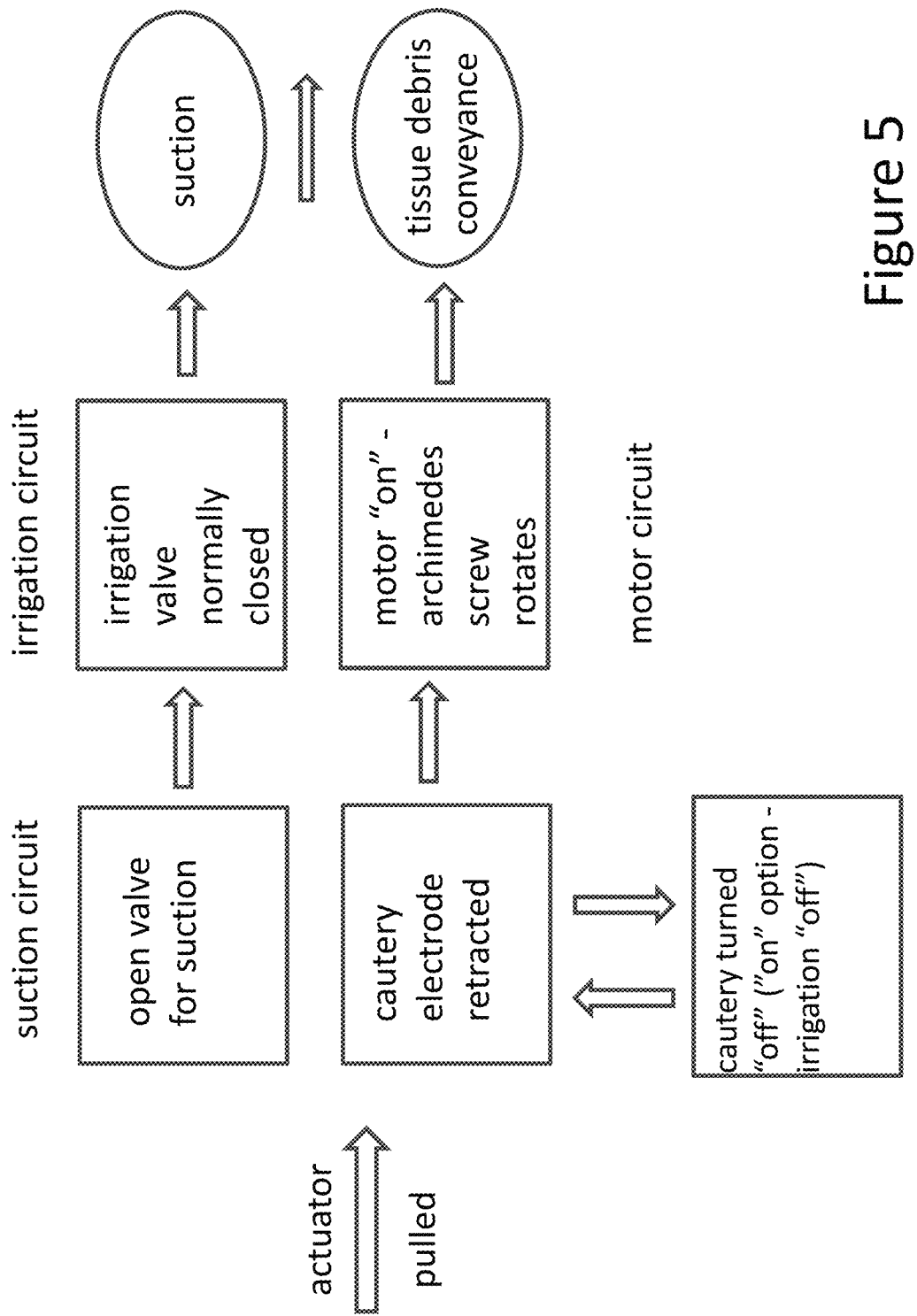
FIG. 5 is a flow chart summarizing how the control system manages the various functions of the device when an actuator is engaged to retract the electrode-screw tool.

As seen in FIG. 5, when the actuator is retracted or pulled back the cautery electrode is retracted and is optionally normally turned off. The cautery electrode may assist in breaking up larger fragments of tissue debris and the control system is optionally configured so that the cautery electrode can be turned "on" when the cautery electrode is a retracted position. This action preferably precludes irrigation from being turned on. As described above with reference to FIG. 4, when the trigger is a retracted position the back end of the cautery electrode physically contacts switch 19 to turn suction on and the motor on. In this manner, the combined effects of suction and conveyance cooperate to reduce the likelihood of tissue debris clogging the cannula 3. This is especially useful for narrow diameter e.g. 5 mm cannulae.

Figure 6:
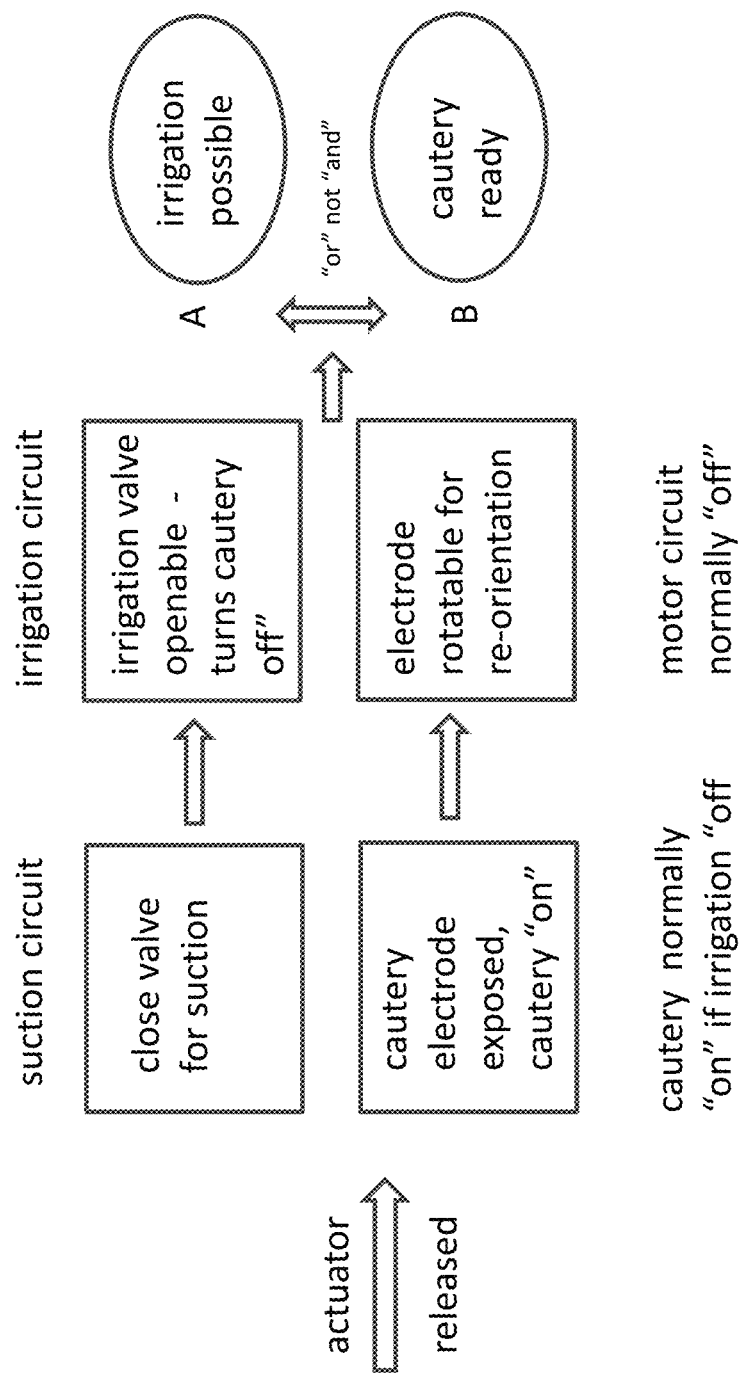
FIG. 6 is a flow chart summarizing how the control system manages the various functions of the device when an actuator is disengaged to re-position the electrode screw tool for cautery functions.

As seen in FIG. 6, release of the trigger re-exposes and turns on the cautery electrode. The control system may accommodate the motor being turned "on" while the cautery electrode is on to rotate and re-orient the cautery electrode tip.

Optionally, the motor 21 and control system provide for motor speed control using for example, a potentiometer (see FIG. 7) so that a slower rotation speed can be used to re-orientate the cautery electrode tip 11a. At least one faster speed may be provided for debris removal. The control system is normally configured to turn the electrode off if the irrigation switch is activated by the user. Accordingly, irrigation option A and cautery option B7 are depicted and described as mutually exclusive alternatives.

Figure 7:
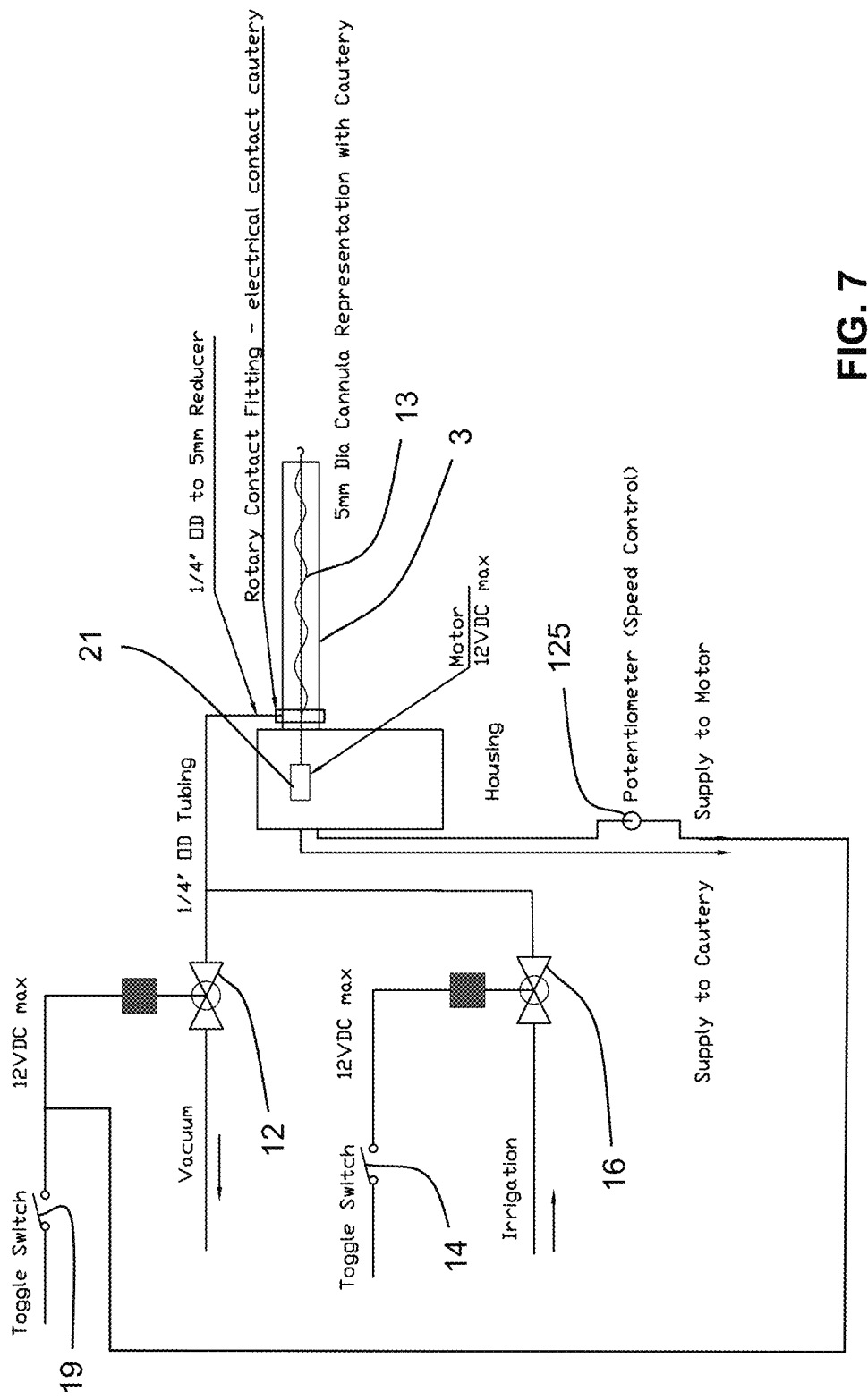
FIG. 7 is a schematic diagram showing key electrical connections of components of the device.

As seen in FIG. 7 at the top left of the Figure a switch corresponding to switch 19 in FIG. 2, is provided to control a solenoid valve for example solenoid valve 12. Switch 19 also controls motor 21 so that that it contemporaneously initiates and terminates suction and rotation of the Archimedes screw. Beneath it is a separate switch corresponding to 14 in FIG. 2 operable to initiate and terminate irrigation. A potentiometer may be used to control the speed of the motor which may be operated by a separate switch. Connection to a power supply optionally in the form of the battery 33 and electrode power supply optionally in the form of a monopolar supply.

The disclosure herein contemplates that the device may be entirely disposable to obviate the cost and effort associated with sterilization of reusable surgical instruments and devices. Such a device may be sold fully assembled so that the connection of these parts to the body portion may be of any type that is secure including adhesive connections that are permanent (i.e. functionally permanent). Alternatively, a fully disposable device may be sold with one or more of the cannula, cautery electrode and Archimedes screw disconnected. These device components can be connected by the user with a form of connection that is either functionally permanent or disconnectable, for example a locking connection. The term locking connection is used to refer to a connection that can be made secure without using an external component such as an adhesive to provide for the secure connection e.g. where one part snaps into another. A disconnectable locking connection might damage the connecting parts, particularly the parts that are intended to be reusable and hence is not considered reusable i.e. designed to be reconnected.

One example of a reusable connector that may be used for connecting an electrode-screw tool in the form in an Archimedes screw instrument with respect to the body portion is shown in FIG. 9. In FIG. 9, the Archimedes screw instrument comprises a first instrument portion 11b (which provides a second Archimedes screw connector), which terminates in an electrode 11k. This instrument portion may be positioned within the cannula is optionally located outside the cannula in the body of device. The first instrument portion 11b is connectable via a female threaded portion 11f to a second instrument portion 11d (11d carries the first Archimedes screw connector and an electrical terminal) optionally positioned within the cannula 3 via a corresponding male threaded portion 11e which has an electrode terminal in the form a mating receptacle 11m.

A cautery electrode that is mounted on the device separately from the Archimedes may be analogously provided with a male end for connection to a second portion of the electrode that is operatively connected to the body of the device.

With reference to one embodiment of a tool or instrument, namely an electrode tool optionally a cautery electrode, an Archimedes screw or a combined Archimedes screw electrode instrument, devices as described herein are to be understood as optionally further comprising proximally positioned portions of the instrument pre-connected to parts of the connector system and distally positioned portions of the instrument that are connectable to the proximally positioned portions. The proximally positioned portions are portions of the instrument that at least partially located within the body of the device. These may be pre-connected to at least one of a drive interface, an electrical connector, a connector operable for connection to the actuator etc. The distally positioned portions may be entirely located outside the body of the device and may connect to proximally positioned portions that extend outside the body of the device. Logistical constraints related to diameters and obstacles (e.g. the implementation of rotating fluid connector) may dictate that the proximally positioned portions of the instrument cannot extend into the body and therefore must be connected distally beyond the body-cannula interface.

The cannula 3 may come attached to body portion. It may also be separate and connectable to the body in a variety of ways e.g. via a standard push-to-connect fitting (also known as an instant fitting).

What is claimed is:

1. A surgical device, comprising:
   a surgical device body;
   a cannula extending from the surgical device body and having a proximal end and a distal end that is insertable into a surgical field within a patient, wherein the cannula defines an axis between the proximal and distal ends, wherein the cannula includes a vacuum port that is fluidically connectable to a vacuum source to draw material from the surgical field through the distal end into the cannula;
   an Archimedes screw positioned within the cannula and rotatable to transport material in the cannula towards the proximal end of the cannula, wherein the Archimedes screw has a hub and a flight; and
   an electrode tool that extends through the hub of the Archimedes screw and is movable between an advanced tool position and a retracted tool position, wherein in the advanced tool position a working end of the electrode tool is outside of the cannula and is energizable to energize tissue in the surgical field, and wherein in the retracted tool position the working end of the electrode tool is positioned axially closer to the proximal end of the cannula than in the advanced tool position so as to permit approach of the distal end of the cannula towards the tissue in the surgical field.

2. The surgical device as claimed in claim 1, wherein the Archimedes screw is axially movable between an advanced screw position within the cannula and a retracted screw position within the cannula, wherein in the advanced screw position a terminal end of the flight is positioned closer to the distal end of the cannula than in the retracted screw position.

3. The surgical device as claimed in claim 2, wherein the electrode tool is connected to the Archimedes screw such that when the screw is in the retracted screw position, the electrode tool is in the retracted tool position.

4. The surgical device as claimed in claim 3, wherein the electrode tool is connected to the Archimedes screw such that when the Archimedes screw is in the advanced screw position, the electrode tool is in the advanced tool position.

5. The surgical device as claimed in claim 1, wherein in the retracted tool position, the working end of the electrode tool is substantially entirely held within the cannula.

6. The surgical device as claimed in claim 5, wherein in the retracted tool position, the working end of the electrode tool is proximate the distal end of the cannula.

7. The surgical device as claimed in claim 1, wherein the electrode tool is a cautery electrode.

8. The surgical device as claimed in claim 7, wherein the cautery electrode extends through the hub of the Archimedes screw.

9. The surgical device as claimed in claim 1, wherein an aperture defining a mouth of the proximal end of the cannula is the vacuum port.

10. The surgical device as claimed in claim 9, wherein a fluid conduit is connectable between the vacuum port and the vacuum source, and further comprises a valve operable to initiate and terminate application of vacuum pressure in the cannula.

11. The surgical device as claimed in claim 1, wherein the vacuum port is a connector provided at the proximal end of the cannula outside the device body, the connector fluidically connectable via a fluid conduit to the vacuum source.

12. The surgical device as claimed in claim 2, wherein the surgical device includes an actuator operable to move the electrode tool between the advanced tool position and the retracted tool position and/or move the Archimedes screw between the advanced screw position and the retracted screw position.

13. The surgical device as claimed in claim 12, wherein the actuator is manually operable to retract at least one of the electrode tool or the Archimedes screw.

14. The surgical device as claimed in claim 13, wherein the actuator is a finger operated lever.

15. The surgical device as claimed in claim 1, wherein the surgical device is a device for performing a laparoscopic surgery in conjunction with a trocar.

16. The surgical device as claimed in claim 1, wherein the surgical device body is configured as a hand-held device.

17. The surgical device as claimed in claim 1, comprising a housing having a cannula connector that is configured to receive the cannula along an axis;
   a drive system that is operable to cause rotation of a drive system output member, wherein the drive system output member has a first Archimedes screw connector that is connectable with a second Archimedes screw connector on the Archimedes screw so as to operatively connect the drive system to the Archimedes screw;
   an electrical terminal that is positioned to electrically connect to the electrode tool; and
   wherein the drive system output member and the electrical terminal are axially movable between the advanced tool position and the retracted tool position relative to the housing.

18. The surgical device as claimed in claim 17, wherein the electrode tool is a cautery electrode and wherein the surgical device is operable to terminate operation of the cautery electrode and to contemporaneously initiate suction and rotation of the Archimedes screw; and wherein the device is operable to initiate operation of the cautery electrode and to contemporaneously terminate suction.

19. The surgical device as claimed in claim 17, wherein the electrical terminal is concentric with the cannula connector and the first Archimedes screw connector is positioned concentrically with respect to the cannula.

20. The surgical device as claimed in claim 17, wherein the drive system comprises a motor located with the housing.

21. A surgical device body, comprising:
   a housing having a cannula connector that is configured to releasably receive a cannula along an axis;
   a drive system that is operable to cause rotation of a drive system output member, wherein the drive system output member has a first Archimedes screw connector that is connectable with a second Archimedes screw connector on an Archimedes screw so as to operatively connect the drive system to the Archimedes screw;
   an electrical terminal that is positioned to electrically connect to a cautery tool that extends through a hub of the Archimedes screw;
   wherein the drive system output member and the electrical terminal are axially movable between an advanced position and a retracted position relative to the housing.

22. The surgical device body as claimed in claim 21, wherein the electrical terminal is concentric with the cannula connector.

23. The surgical device body as claimed in claim 21, wherein the first Archimedes screw connector is positioned concentrically with respect to the cannula.

24. The surgical device body as claimed in claim 23, wherein in the advanced position, the drive system output member and the electrical terminal are positioned to bring the cautery tool to an advanced tool position in which the working end of the cautery tool is outside of the cannula.

25. The surgical device body as claimed in claim 21, further comprising a fluid conduit that has a first conduit end that is fluidically connectable with a vacuum port on the cannula, wherein the fluid conduit is connectable with a vacuum source.

26. The surgical device body as claimed in claim 21, wherein the surgical device body further comprises a control system, the control system operable to control the drive system and to move the drive system output member and the electrical terminal between the advanced position and the retracted position relative to the housing.

27. The surgical device body as claimed in claim 21, further comprising an actuator operable to move the drive system output member and the electrical terminal between an advanced position and a retracted position relative to the housing.

28. The surgical device body as claimed in claim 26, wherein the control system is operable to:
   a) terminate operation of the electrode tool and contemporaneously initiate suction and rotation of the Archimedes screw; and/or
   b) initiate operation of the electrode tool and contemporaneously terminate suction.

29. A method of carrying out a surgical procedure, comprising:
   a) providing a surgical device including a surgical device body, a cannula extending from the body and having a proximal end and a distal end, an Archimedes screw positioned in the cannula and having a hub and a flight, and an electrode tool that extends through the hub;
b) inserting the cannula into a surgical field in a patient;
c) providing the electrode tool in an advanced tool position in which a working end of the electrode tool is outside of the cannula;
d) energizing tissue in the surgical field with the working end of the electrode tool;
e) moving the electrode tool to a retracted tool position in which the working end of the electrode tool is positioned axially closer to the proximal end of the cannula than in the advanced tool position;
f) manipulating the surgical device to bring the distal end of the cannula towards the tissue in the surgical field;
g) applying a negative pressure in the cannula so as to draw material from the surgical field through the distal end into the cannula;
h) rotating the Archimedes screw to transport material in the cannula towards the proximal end of the cannula.

\* \* \* \* \*